(12) United States Patent
Kraeuter et al.

(10) Patent No.: US 12,139,279 B1
(45) Date of Patent: Nov. 12, 2024

(54) VISUAL INSPECTION POSABLE INVERTEBRATE ROBOT (VIPIR) SYSTEM

(71) Applicant: United States of America as represented by the Administrator of NASA, Washington, DC (US)

(72) Inventors: Jonathan Kraeuter, Beltsville, MD (US); Matthew Ashmore, Beltsville, MD (US); Michael Cortina, Beltsville, MD (US); Syed-Ali Husain, Beltsville, MD (US); Ross Henry, Greenbelt, MD (US); James Biesinger, Beltsville, MD (US); Edward Cheung, Beltsville, MD (US)

(73) Assignee: United States of America as represented by the Administrator of NASA, Washington, DC (US)

( * ) Notice: Subject to any disclaimer, the term of this patent is extended or adjusted under 35 U.S.C. 154(b) by 1213 days.

(21) Appl. No.: 16/877,713

(22) Filed: May 19, 2020

(51) Int. Cl.
*B64G 4/00* (2006.01)
*B65H 75/44* (2006.01)
*G02B 23/24* (2006.01)
*H04N 23/54* (2023.01)
*A61B 1/00* (2006.01)
*A61B 1/005* (2006.01)
(Continued)

(52) U.S. Cl.
CPC .......... *B64G 4/00* (2013.01); *B65H 75/4471* (2013.01); *B65H 75/4486* (2013.01); *G02B 23/2484* (2013.01); *H04N 23/54* (2023.01); *A61B 1/0005* (2013.01); *A61B 1/005* (2013.01); *A61B 1/008* (2013.01); *A61B 1/05* (2013.01); *B65H 2403/42* (2013.01); *H04N 23/555* (2023.01)

(58) Field of Classification Search
CPC .... E21B 47/002; H04N 7/185; G03B 37/005; A61B 1/005–07; G02B 23/2492; G02B 23/2484; G02B 23/2476; G02B 23/24; B64G 4/00; B65H 75/02–486
See application file for complete search history.

(56) References Cited

U.S. PATENT DOCUMENTS 5,801,825 A * 9/1998 Nutter ................ G02B 23/2492
356/241.1
5,903,306 A * 5/1999 Heckendorn ........ G03B 37/005
348/42
(Continued)

FOREIGN PATENT DOCUMENTS

DE 102016113406 B4 * 2/2022 ........... F01D 21/003
GB 2606728 A * 11/2022 ............. A61B 17/32

OTHER PUBLICATIONS

Machine Translation of DE 102016113406 (Year: 2016).*

*Primary Examiner* — Nathaniel J Kolb
(74) *Attorney, Agent, or Firm* — Derek J. Langdon; Matthew F. Johnston; Trenton J. Roche

(57) ABSTRACT

A visual inspection posable invertebrate robot (VIPIR) borescope camera system can inspect components in difficult to reach locations. The system enables dexterous robotic inspection of worksites and areas that were heretofore impossible to inspect via extravehicular activities (EVA) and fixed situational awareness cameras. VIPIR may include: (1) a main drive assembly; (2) a reel system; (3) a video borescope assembly (VBA); (4) an enhanced motorized zoom lens (EMZL); (5) a fixed camera assembly (FCA); (6) a support structure; and/or (7) a main electronics box (MEB).

13 Claims, 29 Drawing Sheets

(51) Int. Cl.
 *A61B 1/008* (2006.01)
 *A61B 1/05* (2006.01)
 *H04N 23/50* (2023.01)

(56) References Cited

U.S. PATENT DOCUMENTS

| | | | | |
|---|---|---|---|---|
| 2005/0131279 | A1* | 6/2005 | Boulais | A61B 1/0016 |
| | | | | 600/141 |
| 2007/0125962 | A1* | 6/2007 | Okabe | H01L 21/67109 |
| | | | | 250/492.1 |
| 2015/0119638 | A1* | 4/2015 | Yu | A61B 90/30 |
| | | | | 600/102 |
| 2021/0254500 | A1* | 8/2021 | Bifulco | B08B 9/0321 |

* cited by examiner

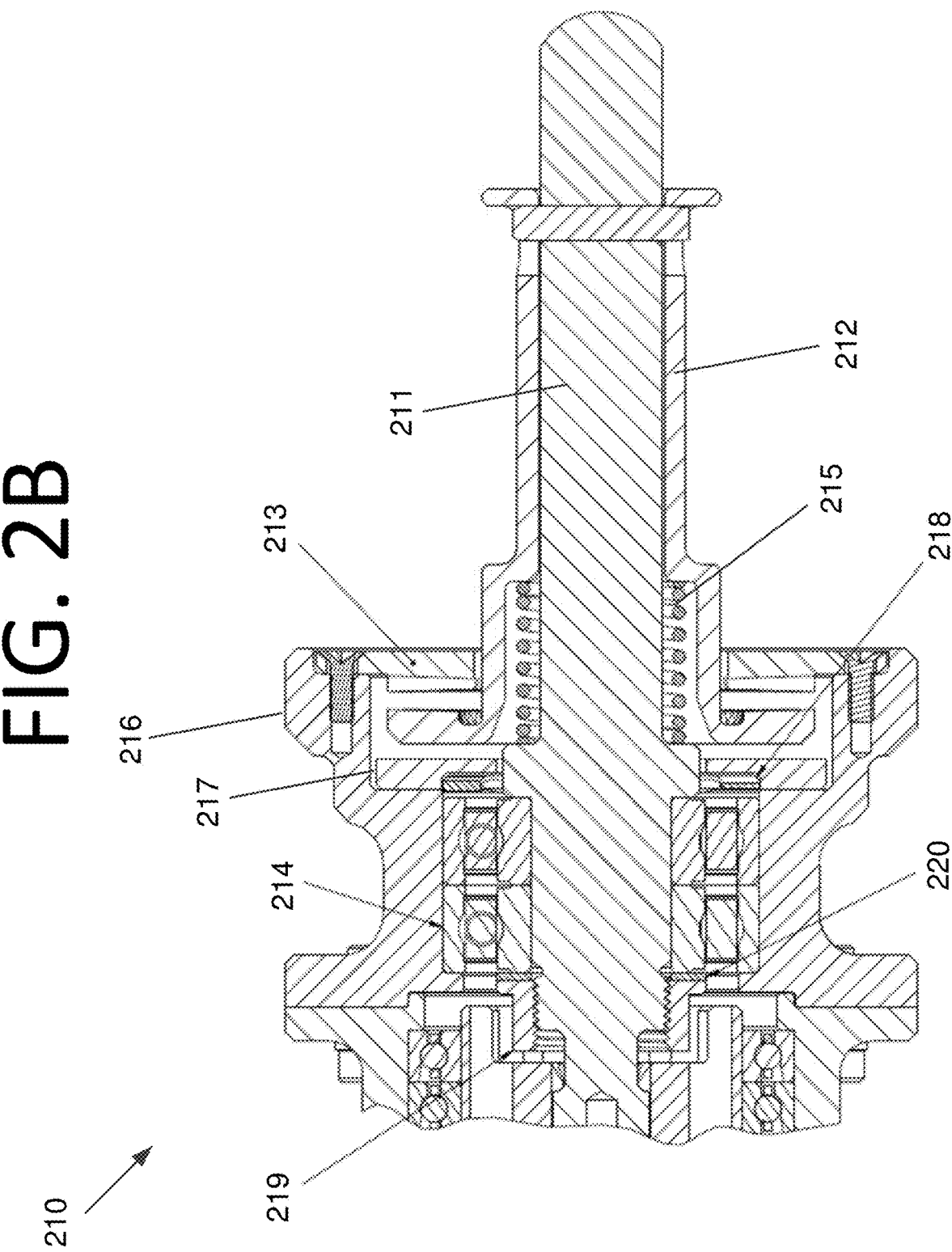

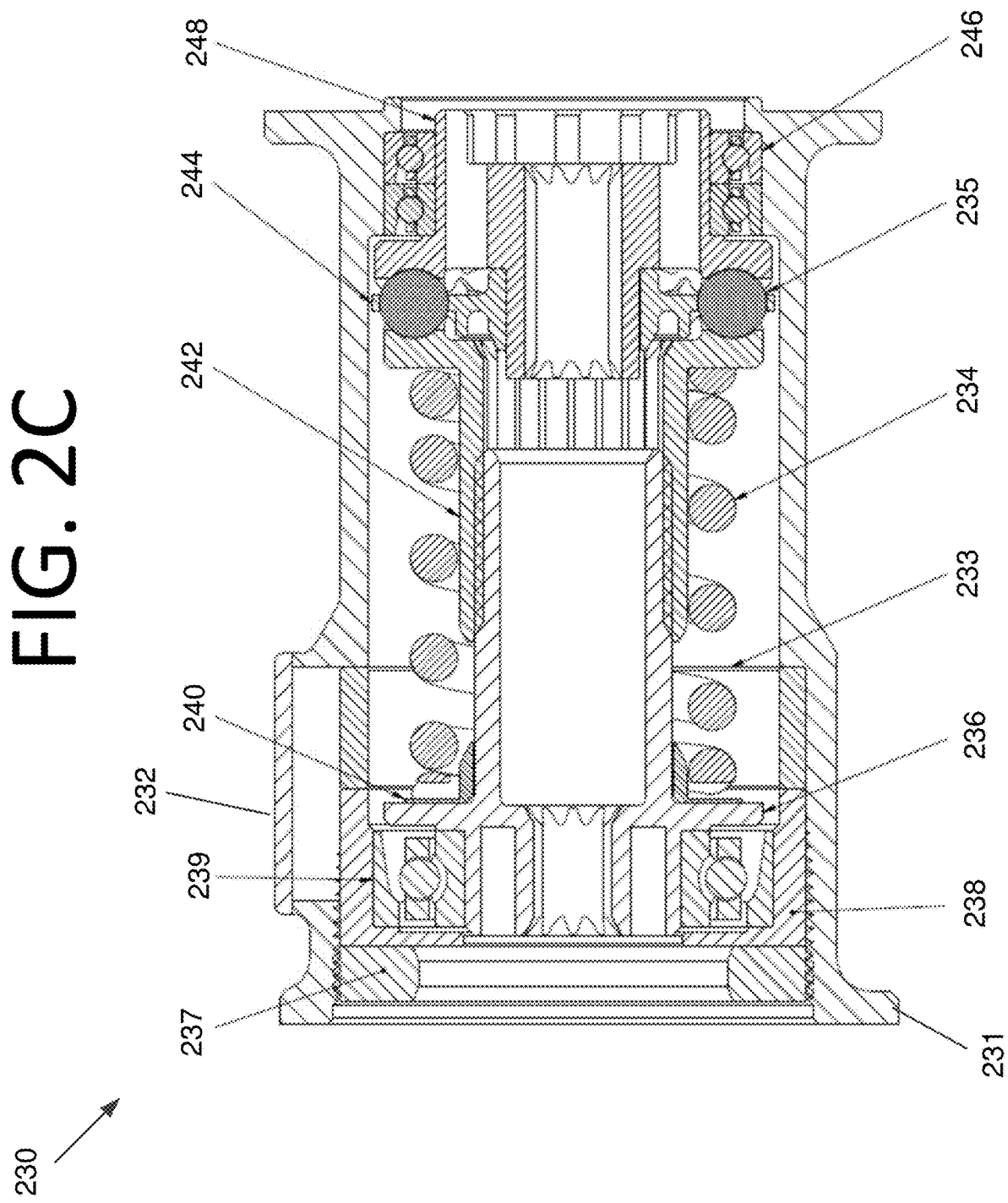

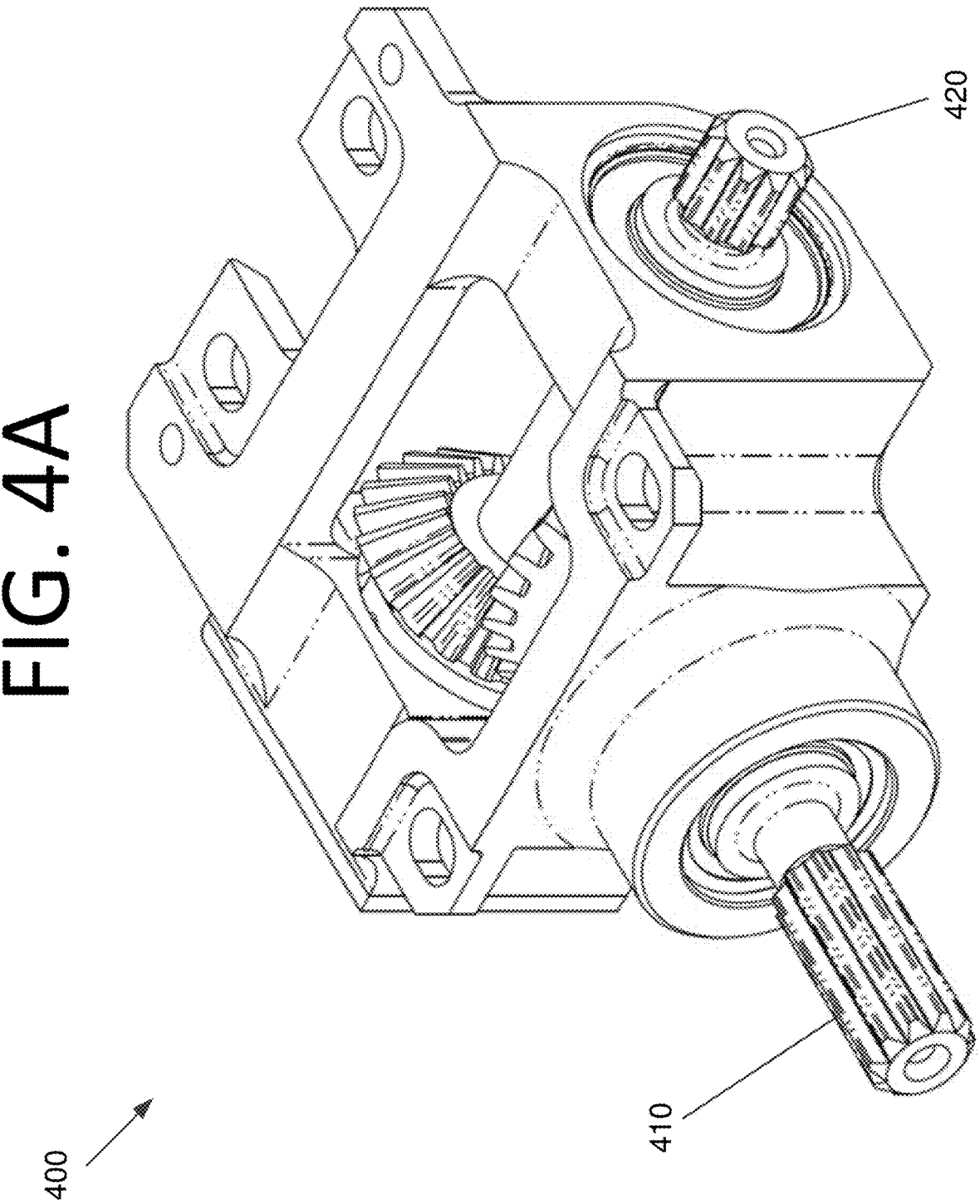

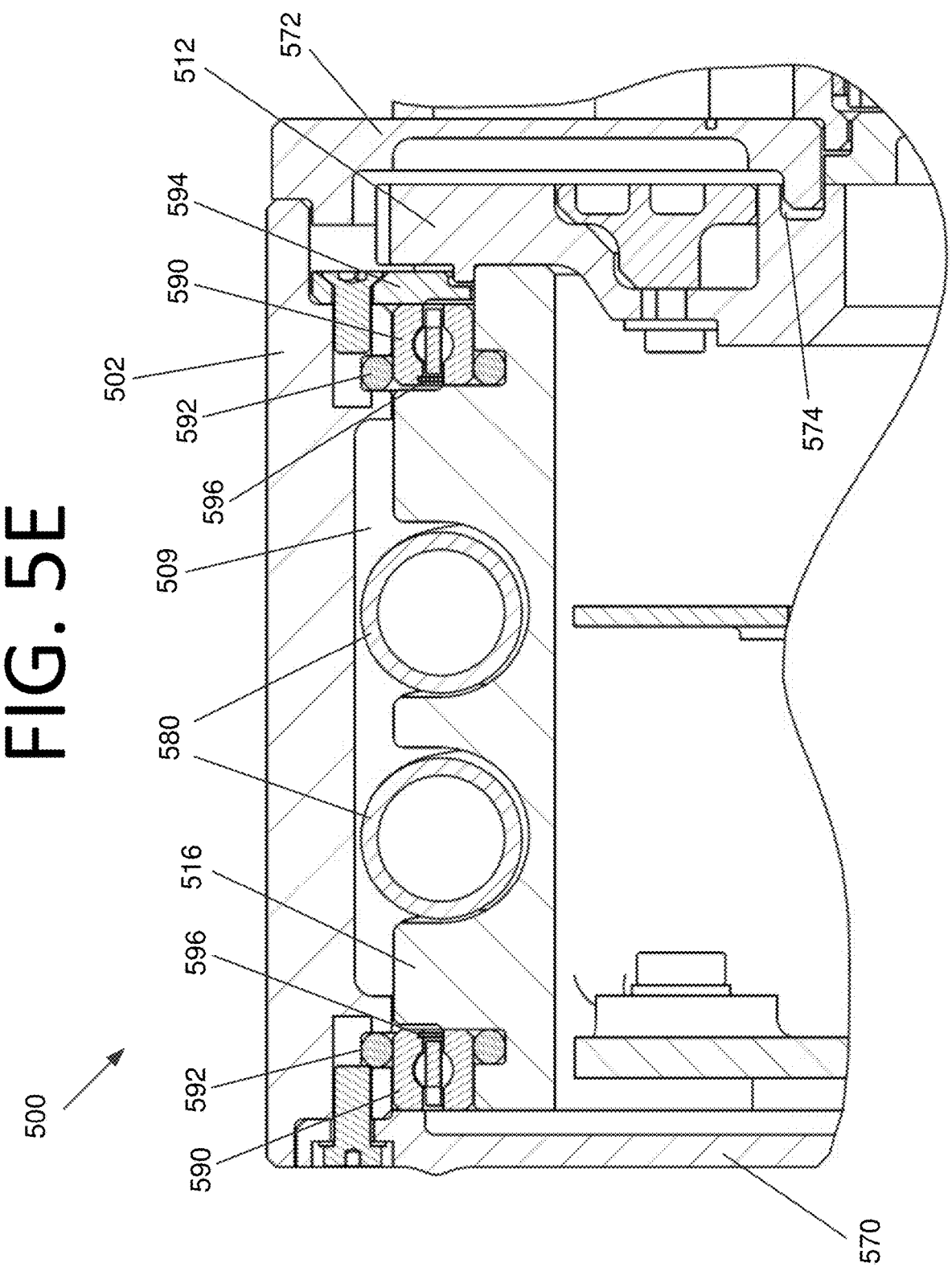

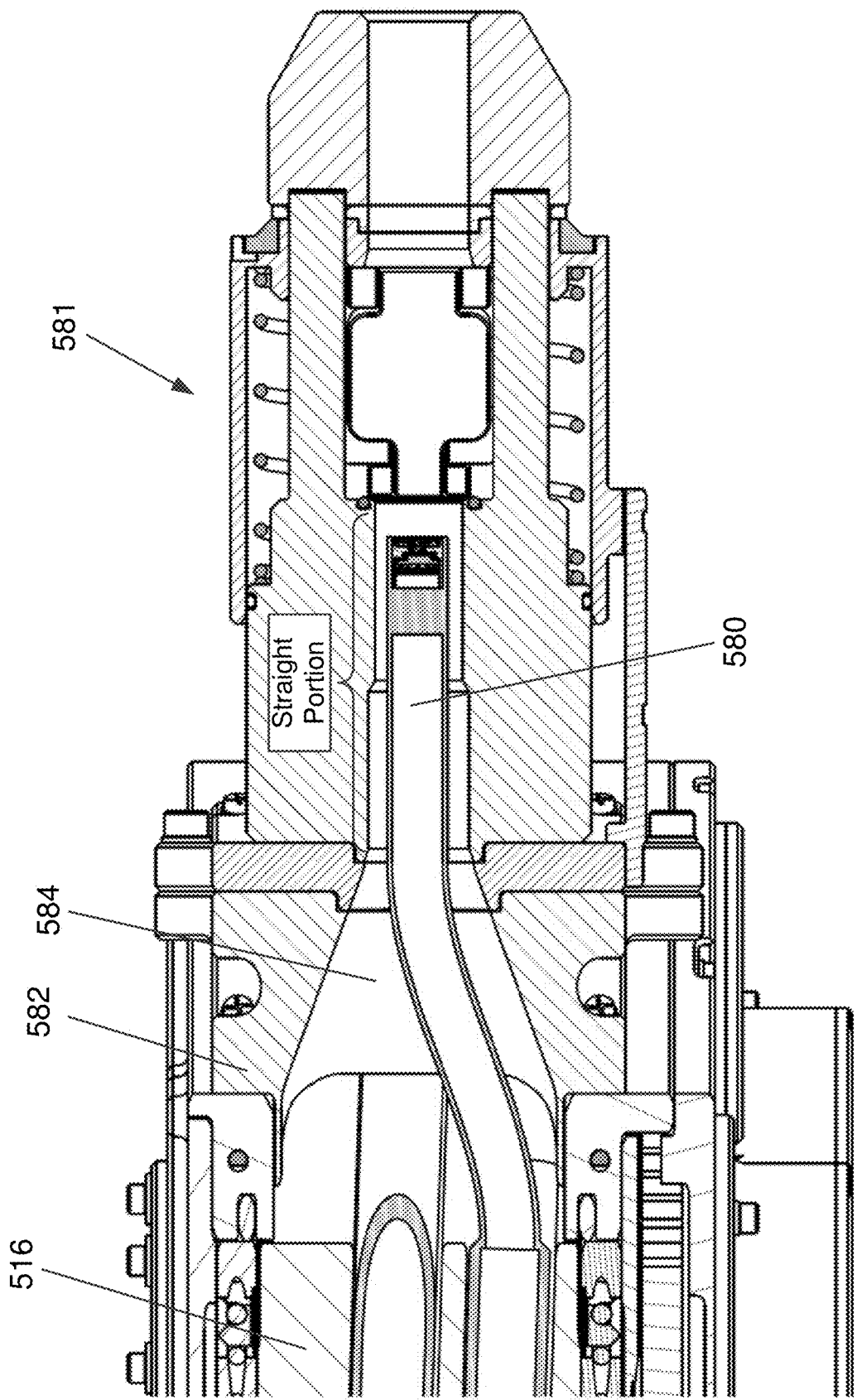

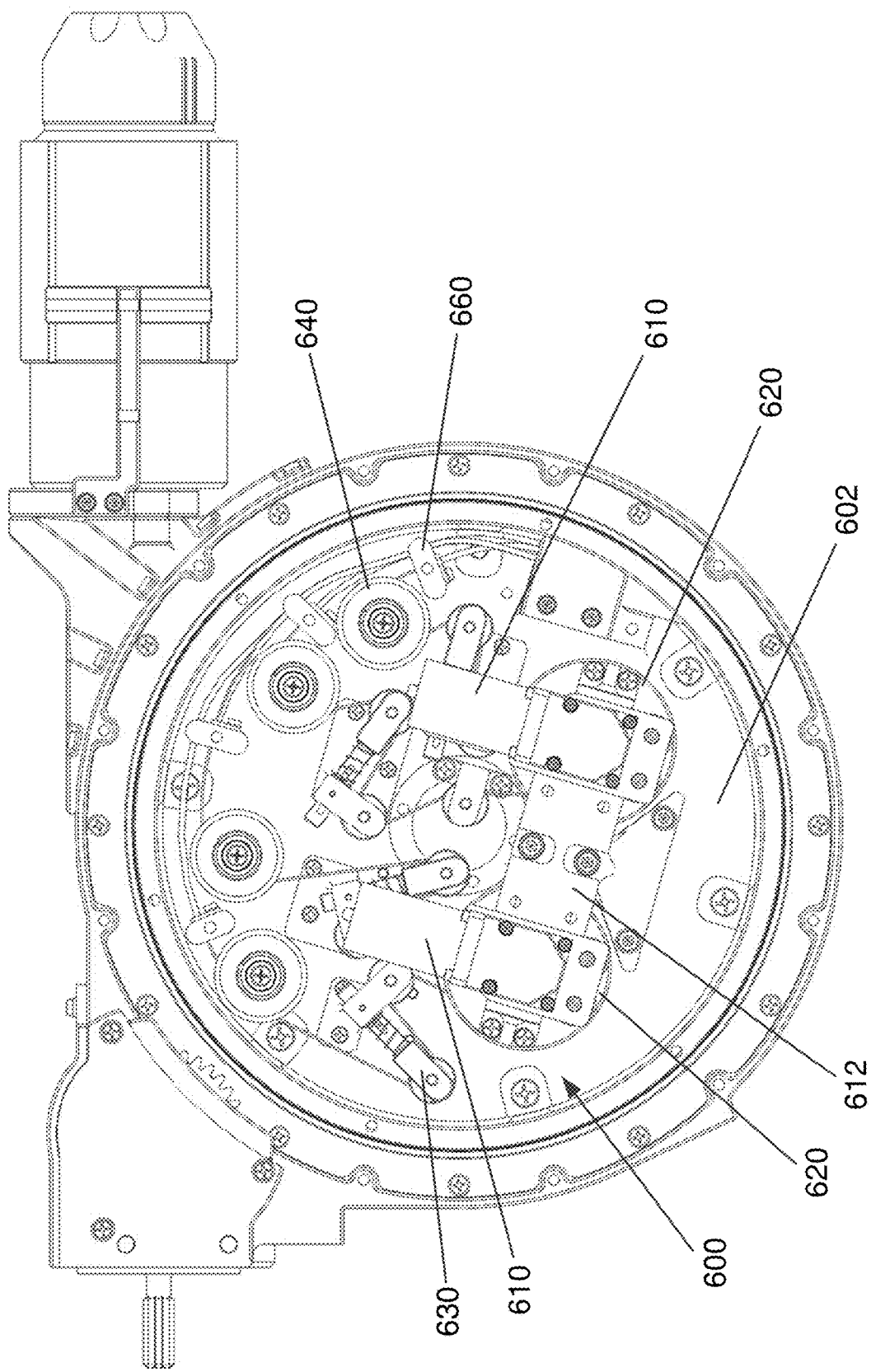

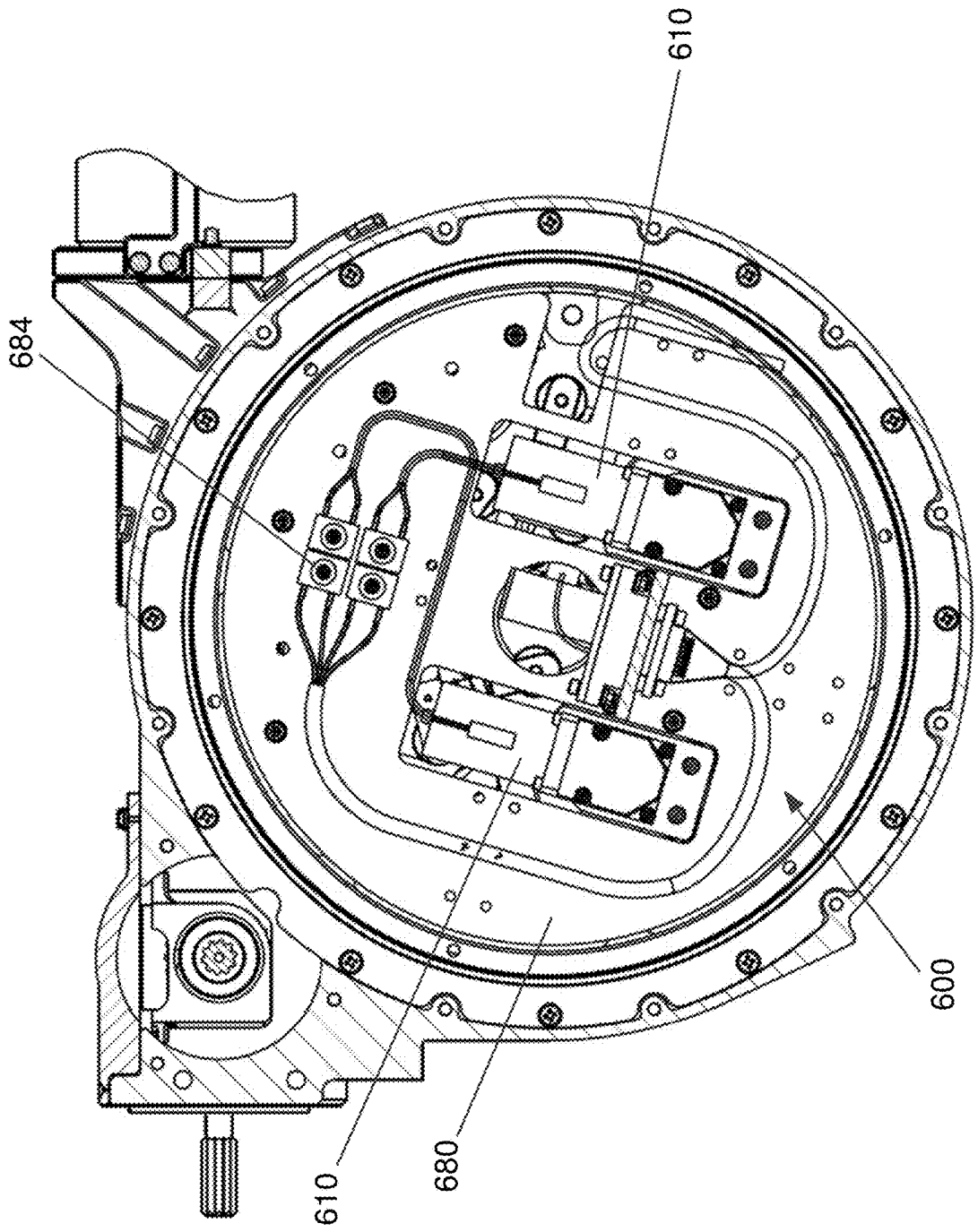

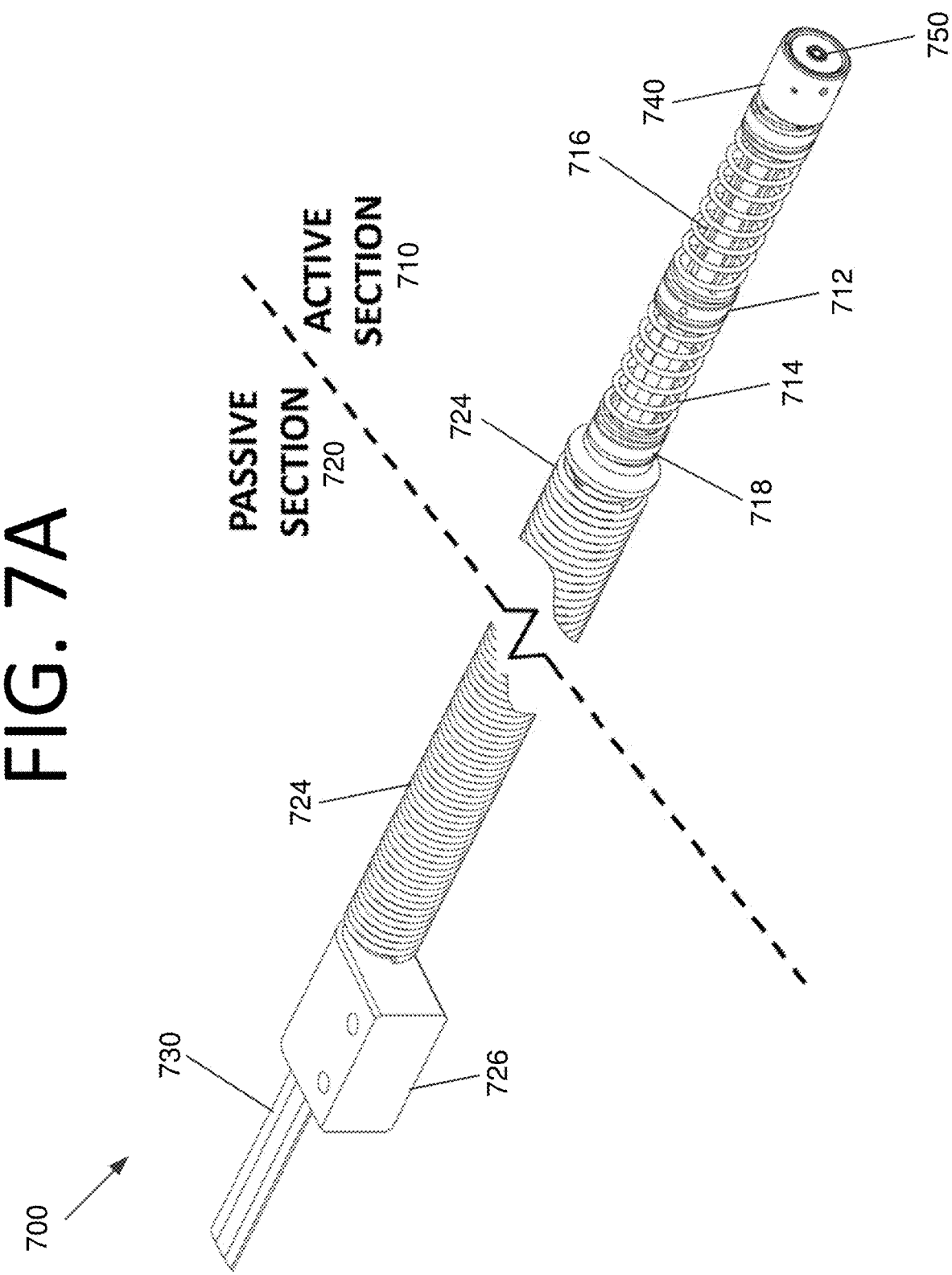

ically operated servicing activities, it is important for the robot operator to visually assess the state of the client, worksite, robot manipulator, and robotic tools during each step of a servicing operation.
VISUAL INSPECTION POSABLE INVERTEBRATE ROBOT (VIPIR) SYSTEM

STATEMENT OF FEDERAL RIGHTS

The invention described herein was made by employees of the United States Government and may be manufactured and used by or for the Government for Government purposes without the payment of any royalties thereon or therefore.

FIELD

The present invention generally relates to inspection robotics, and more specifically, to a robotic borescope camera system that can inspect components in difficult to reach locations.

BACKGROUND

Inspecting and servicing spacecraft presents unique challenges. For instance, technical challenges posed by tele-operated robotic satellite servicing include the need to perform reconnaissance, inspection, or visual verification of a potential worksite or client that may not be accessible or visible due to poor lighting (visibility restriction), confined or limited access due to the size of the worksite or entry to the worksite (size restriction), placement beyond the limits of manipulator arm reach (reach restriction), necessity to maintain robotic manipulator at a certain threshold distance from the worksite in order to avoid impact due to dynamic motion of the manipulator or the client (distance restriction), and placement in an area requiring more degrees of freedom to access than are available from the manipulator (dexterity restriction). In the context of telerobotically operated servicing activities, it is important for the robot operator to visually assess the state of the client, worksite, robot manipulator, and robotic tools during each step of a servicing operation.

Visibility Restrictions

In telerobotic operation, lighting quality is more important than overall brightness and should be uniquely tuned to the camera and lens being used. Ambient lighting may be of insufficient intensity to allow a useful image to be generated. Conversely, the lighting may be too bright, which causes the image to oversaturate, bloom, or wash out. A well-designed camera system typically requires optimization for a specific purpose via carefully designed light baffles, electronic settings, and iris diameter. This camera system should then be complimented with a dedicated, tuned light source that helps deliver the right amount of light at the right distance.

Size Restrictions

Often, the object being accessed or manipulated may lie in an area that is not accessible to the robotic manipulator arm. For example, in a representative satellite servicing scenario, a valve or electrical connector requiring servicing may lie within the body of a spacecraft. The access to this device may be only through a small panel or door, or behind some structural truss members, and the openings may be too small for a robot end-effector to penetrate. In another example, a spacecraft propulsion or cooling system component may lie within the network of the spacecraft plumbing, and the only way to inspect the target feature is to insert a camera into the piping. In a third example, a stuck solar array or partially-deployed antenna may lie against the body of the spacecraft, and in order to inspect the hinge, launch restraint, or other suspected faulty component, a small camera must be inserted underneath the panel or antenna boom.

Reach Restrictions

In certain cases, the worksite or component requiring inspection is beyond the reach of the manipulator arm, due either to the length limit of the arm itself, or more commonly, the inability of the arm joints to achieve an appropriate position of the end effector without hitting a joint limit or singularity. This situation requires a new appendage that is capable of augmenting the kinematically achievable positions of the end effector.

Distance Restrictions

Under certain circumstances in a servicing scenario, or during robotic activities on the International Space Station (ISS), a certain distance must be maintained between the end effector of the robotic manipulator arm and the worksite in order to allow for dynamic motion of the end effector without impacting the worksite. This distance may be too little or too great, for a camera with a fixed focal length lens, to render a useful video image, due to the mismatch in lens focal length and focus settings. In order to circumvent this problem, a camera must be extended to the worksite, or the camera must be equipped with adjustable zoom and focus with a range sufficient to cover the distance to the target and focus properly on that target. The problem is exacerbated during autonomous rendezvous and proximity operations (RPO), in which one spacecraft attempts to dock with another. In this case, the docking craft must visualize the docking interfaces of the target in order to measure distance and orientation.

The docking event starts at a great distance from the target, and finishes extremely close, requiring substantial range in a zoom and focus mechanism. Because the distance is changing during the entire docking event, the camera system requires adjustable zoom and focus control with a fast response rate. Prior to any servicing event, the servicing spacecraft would perform a reconnaissance activity around the perimeter of the client spacecraft at a substantial distance. This survey allows the servicer to collect data on the overall external condition of the client, as well as verify the state of machine vision and docking interfaces. Due to the distance at which this survey is conducted, a camera with substantial zoom capability is required.

Dexterity Restrictions

A worksite may lie in an area that requires more degrees of freedom to access than are available from the joints of the manipulator arm. Examples are components that lie on a hidden or recessed surface, beneath or between surfaces, or on a surface opposite the entry direction (i.e. the manipulator needs to enter into a volume and then turn 180° to look backwards within that volume).

Accordingly, an improved robotic inspection system may be beneficial.

SUMMARY

Certain embodiments of the present invention may provide solutions to the problems and needs in the art that have not yet been fully identified, appreciated, or solved by conventional robotic inspection technologies. For example, some embodiments pertain to a robotic borescope camera system that can inspect components in difficult to reach locations.

In an embodiment, a visual inspection posable invertebrate robot (VIPIR) system includes a reel system includes a main housing, a rotating assembly that includes a spool and a reel gear, a tendon management system (TMS), and a twist capsule. The VIPIR system also includes a video borescope assembly (VBA) that is operably connected to, and deployable by, the reel system. The VBA includes a camera and a plurality of tendons. The VIPIR system further includes a seal system operably connected to the reel system. The seal system is configured to engage with a service port and allow the VBA to pass therethrough.

In another embodiment, a reel system includes a main housing that includes an inner bore, a rotating assembly that includes a spool, and a TMS. The spool includes helical grooves. A VBA is constrained between the inner bore of the main housing of the reel system and the helical grooves of the spool.

In yet another embodiment, a VBA includes a plurality of tendons and a respective guide tube for each tendon. The VBA also includes an active section that can be articulated once the VBA is deployed. The active section includes a head that houses a camera and provides a termination point for the tendons. The VBA further includes a passive section that is not articulated. The passive section is operably connected to the active section and a TMS.

BRIEF DESCRIPTION OF THE DRAWINGS

In order that the advantages of certain embodiments of the invention will be readily understood, a more particular description of the invention briefly described above will be rendered by reference to specific embodiments that are illustrated in the appended drawings. While it should be understood that these drawings depict only typical embodiments of the invention and are not therefore to be considered to be limiting of its scope, the invention will be described and explained with additional specificity and detail through the use of the accompanying drawings, in which:

FIG. 2B is a cross-section view illustrating the anti-rotation device (ARD) of FIG. 2A, according to an embodiment of the present invention.

FIG. 2C is a side cross-section view illustrating the mechanical torque limiter (TL) of FIG. 2A, according to an embodiment of the present invention.

FIG. 4A is a perspective view illustrating a right-angle gearbox (RAGB), according to an embodiment of the present invention.

FIG. 5E is a side cross-section view illustrating internal components of the reel system, according to an embodiment of the present invention.

FIG. 5F is a top cross-section view of a portion of the reel system, including the seal system, from which the VBA extends out from and is retracted back into the reel system, according to an embodiment of the present invention.

FIG. 6A is a right side cutaway view illustrating a tendon management system (TMS) within a rotating assembly, according to an embodiment of the present invention.

FIG. 6D is a right side cross-section view illustrating a harness blockoff plate, according to an embodiment of the present invention.

FIG. 7A is a segmented perspective view illustrating the VBA, according to an embodiment of the present invention.

DETAILED DESCRIPTION OF THE EMBODIMENTS

Some embodiments of the present invention pertain to a robotic borescope camera system that can inspect components in difficult to reach locations. The VIPIR system of some embodiments is a multi-camera device that enables dexterous robotic inspection of worksites and areas that were heretofore impossible to inspect via extravehicular activities (EVA) and fixed situational awareness cameras. Some embodiments of VIPIR are designed to be used by the ISS dexterous robotic system (SPDM/DEXTRE) and receive both mechanical and electrical services from the Special Purpose Dexterous Manipulator (SPDM) Orbital Replacement Unit (ORU)/Tool Changeout Mechanism (OTCM) in order to power its camera systems and transmit video back to the ground.

VIPIR in some embodiments is grasped by the SPDM OTCM and maneuvered to the worksite, where it can inspect using a fixed-mount, adjustable zoom and focus camera, whose positioning is limited only by the extents of the SPDM arm or deploy a flexible, small diameter, articulating borescope camera that can be steered in four orthogonal directions at any deployed length. Both cameras may provide color video and carry on-board LED illumination arrays for operation in dark, confined areas. The combination of the adjustable zoom/focus camera and the articulating borescope in some embodiments yields a visualization platform that is unparalleled in its versatility and adaptability to difficult-to-access worksites. However, embodiments of VIPIR are not limited to ISS applications, and some embodiments may be used for terrestrial missions, satellite servicing missions in low Earth orbit (LEO) or geosynchronous orbit (GEO), deep space missions, or for any other suitable application without deviating from the scope of the invention.

Figure 1A:
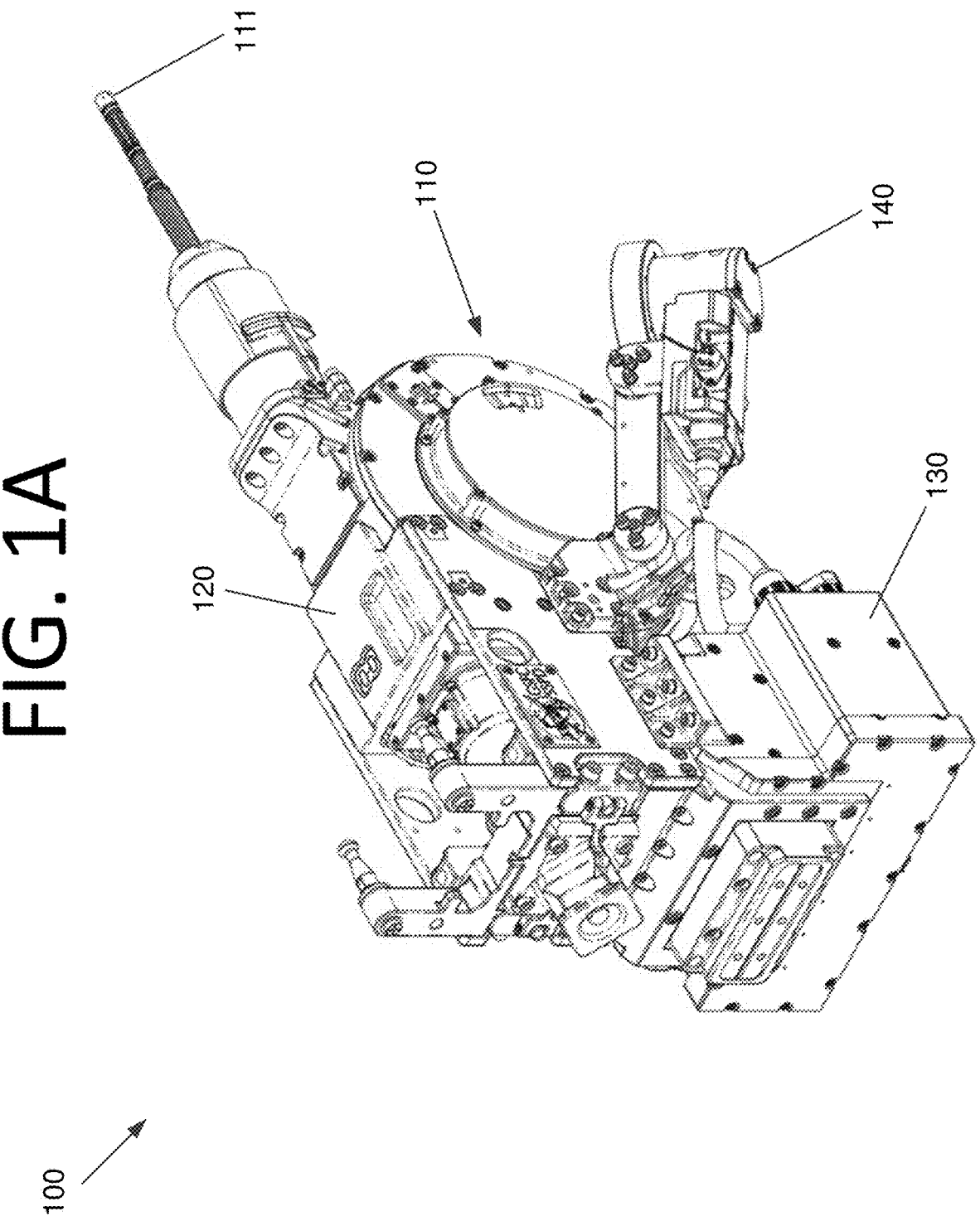
FIG. 1A is a right side perspective view illustrating a visual inspection posable invertebrate robot (VIPIR) system, according to an embodiment of the present invention.

Some embodiments of VIPIR include seven major subassemblies: (1) a main drive assembly; (2) a reel system; (3) a video borescope assembly (VBA); (4) an enhanced motorized zoom lens (EMZL) camera; (5) a fixed camera assembly (FCA); (6) a support structure; and (7) a main electronics box (MEB). Such an embodiment is shown in VIPIR 100 of FIGS. 1A and 1B. VIPIR 100 includes a mechanical assembly 110 that contains deployment and articulation mechanisms for the borescope camera and a sealing mechanism (see FIG. 1C). VIPIR 100 also includes a support structure 120 that provides universal robotic refueling mission (RRM) stowage interfaces and a supporting structure for mechanical assembly 110 and MEB 130. MEB 130 includes the motor controller, power conditioning, telemetry, video processing unit, camera selector, Wi-Fi, lighting, and heater electronics.

MEB 130 is the nerve center of VIPIR and provides the electrical interface to the OTCM. MEB 130 includes the motor controller, which drives the tendon motors that articulate the VBA, drives the zoom and focus motors on the EMZL camera, and provides a communications interface for remote commanding and telemetry acquisition through the communications bus. MEB 130 also includes video processing electronics for each of the VIPIR NTSC camera feeds (e.g., National Television System Committee (NTSC) video, color, video graphics array (VGA) (640×480)): the EMZL camera, the FCA camera, and the VBA camera. The video processing electronics are responsible for both converting the standard NTSC video into ISS-compatible NTSC video and selecting a single video stream output to relay through the OTCM video system downlink to the operator on the ground in some embodiments. The video processing electronics may also be capable of transmitting native high definition (HD) video (1280×720 pixels) from the VBA camera over Wi-Fi to wireless receivers on the ISS. MEB 130 also provides power for the camera LED arrays and the VIPIR active thermal control system.

VIPIR 100 further includes an FCA 140 and an EMZL 150. Also included is a VBA 111 of mechanical assembly 110. FCA 140 is a situational awareness camera (e.g., NTSC video, color, VGA (640×480)) that provides a view of the front end of the tool and various visual indicators in order to position the tool to the worksite and deploy VBA 111. EMZL 150 is a mid-range inspection camera (e.g., NTSC, color, VGA (640×480)) that provides a view of the target using motorized 12-36 mm optical zoom and focus capabilities, for example. However, any desired optical zoom and focus capabilities may be used without deviating from the scope of the invention. VBA 111 includes a miniaturized close-range inspection camera (e.g., digital, color, HD (1280×720)) that can be deployed into a close-quarters worksite, and provide a view of a hard-to-reach target using miniaturized optics, a high resolution sensor, associated camera electronics, and integrated lighting.

Figure 1B:
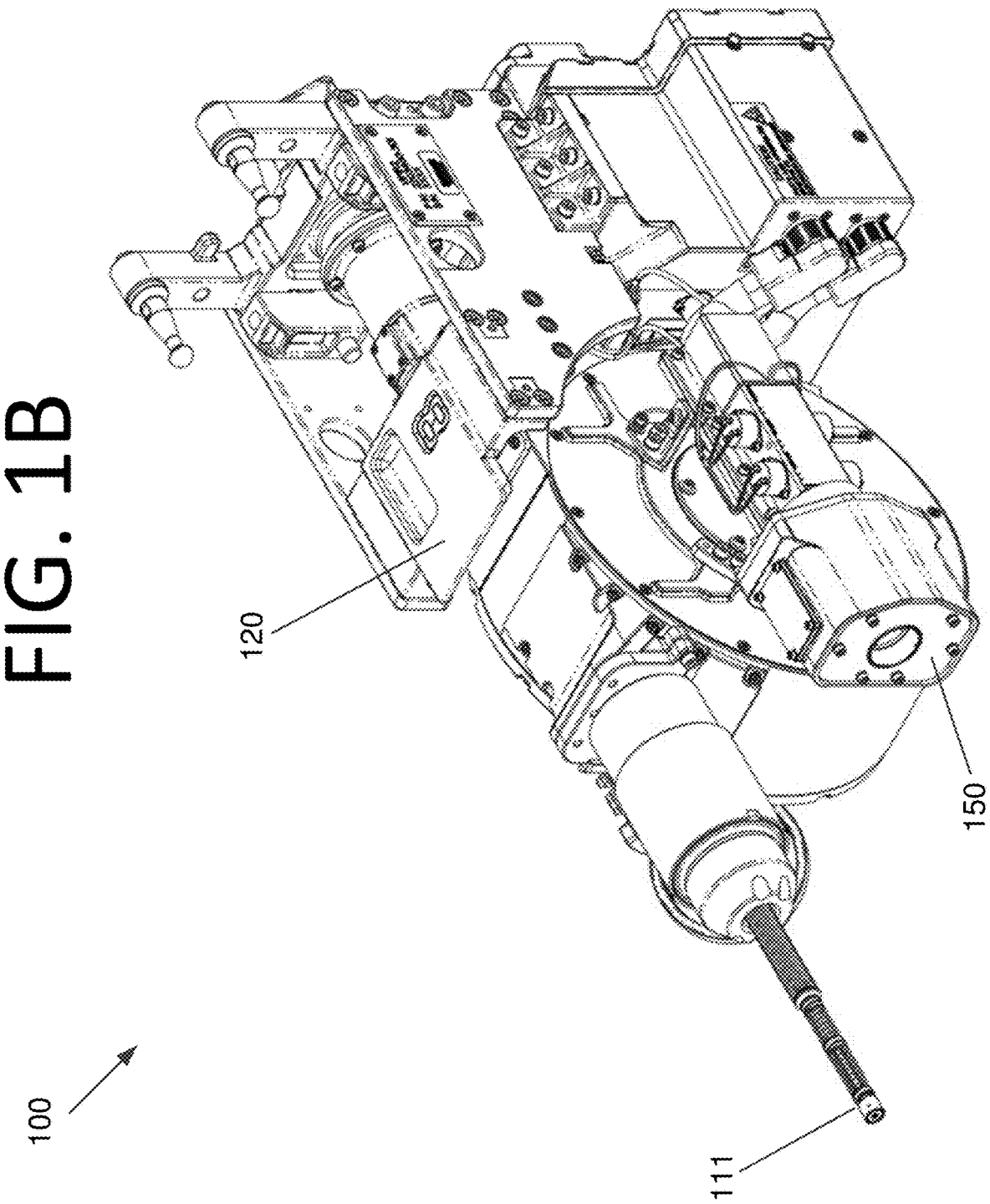
FIG. 1B is a left side perspective view illustrating the VIPIR system of FIG. 1A, according to an embodiment of the present invention.
Figure 1C:
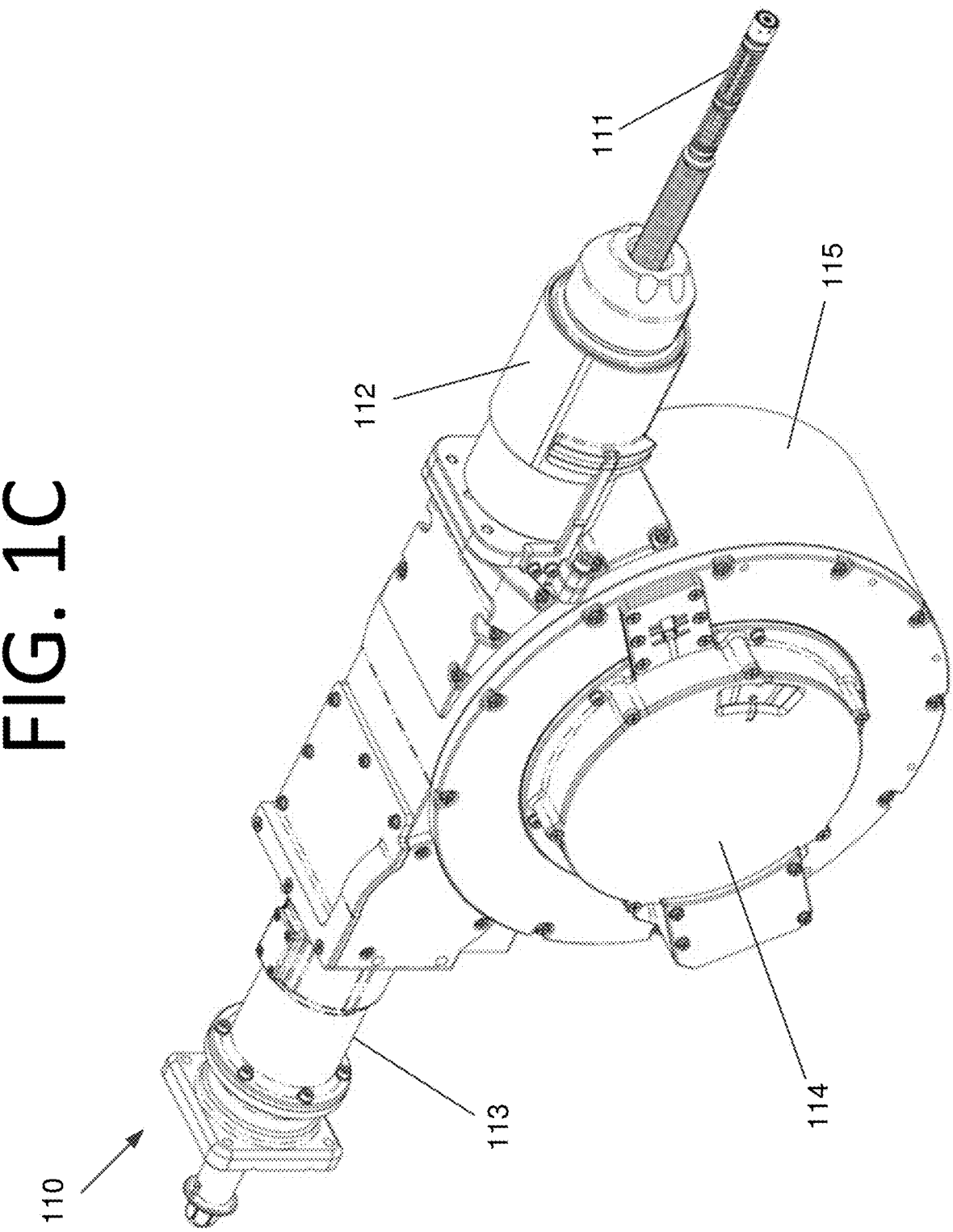
FIG. 1C is a right side perspective view illustrating a mechanical assembly, according to an embodiment of the present invention.

Turning to FIG. 1C, mechanical assembly 110 also includes a seal system 112, a main drive assembly 113, a twist capsule 114, and a reel system 115. Seal system 112 contains an external seal that forms a seal at the service port and an internal seal that protects the borescope camera of VBA 111. Main drive assembly 113 in this embodiment contains an OTCM 7/16" hex drive interface, an anti-rotation device (ARD), and a torque limiter (TL). Twist capsule 114 includes a flexible printed circuit board (flex) harness that transmits borescope camera and motor signals over a rotating interface. Reel system 115 includes a right-angle gearbox (RAGB) and gear system that deploy VBA 111 and a tendon management system that controls articulation of the tip of VBA 111.

Main Drive Assembly

Figure 2A:
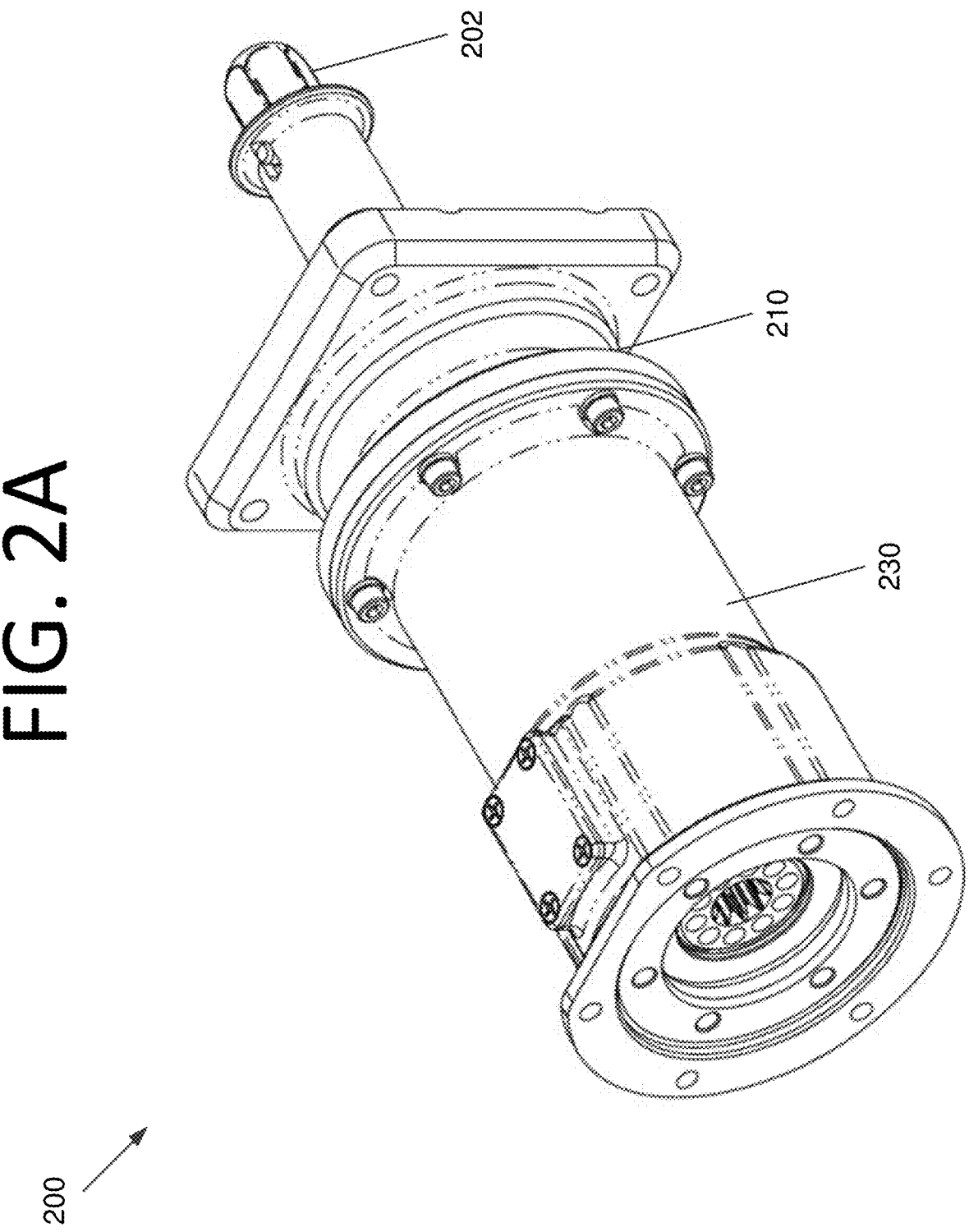
FIG. 2A is a perspective view illustrating a main drive assembly, according to an embodiment of the present invention.

FIG. 2A is a perspective view illustrating a main drive assembly 200, according to an embodiment of the present invention. Main drive assembly 200 includes a robotic hex drive interface 202, an ARD 210, and a mechanical TL 230. Hex drive interface 202 receives torque from a mechanical torquer (e.g., an OTCM mechanical torquer), and through on-board TL 230, translates the input torque into deployment and retraction of the VBA via a reel system.

In some embodiments, the TL is able to achieve an unheard of 10% torque accuracy from −60° C. to 100° C. The TL of some embodiments protects the VBA deployment mechanism and the VBA tendons from overload if the VBA becomes bound or encounters one of its hard stops with too much input torque from the OTCM. The TL may be a mechanical-detent style device that incorporates an array of rolling balls disposed between two opposed scalloped clutch disks, clamped together via a preload spring which determines the slip torque. The torque limiter may transmit an input torque with zero backlash until the calibrated slip torque is reached, at which point a separating force between the clutches is generated that overcomes the spring preload, causing the input clutch to rotate relative to the output clutch and advance the ball array to the next set of detents in each clutch disk. The profile of the clutch teeth may be designed such that the maximum slip torque is achieved at the moment of first relative motion between the clutches, which ensures no torque variance between detents. The assembly may be designed such that the balls always exhibit rolling contact against the clutch teeth, which has allowed the torque limiter test unit to demonstrate nearly 500,000 slip cycles with no appreciable wear and no loss of accuracy.

Some embodiments of VIPIR feature a unique ARD that prevents the reel system from inadvertently deploying the VBA under launch loads or when thermally cycled during long-term stowage. The ARD capitalizes on the need to extend the OTCM torquer in order to engage the mechanical drive of the tool in some embodiments. During launch and while stowed, the ARD teeth may engage a mating, opposed, toothed plate with spring preload. When the OTCM torquer engages the tool, its socket may depress a collar, which causes the ARD teeth to separate, unlocking the drive.

FIG. 2B is a cross-section view illustrating ARD 210 of FIG. 2A, according to an embodiment of the present invention. ARD 210 includes a main shaft 211 that couples ARD 210 to a mechanical torquer via hex drive interface 202. A locking collar 212 is actuated by the edge of the socket of the mechanical torquer. A locking plate 213 interfaces with locking collar 212 via mechanical teeth, for instance. Bearings 214 allow for smooth rotation of shaft 211.

A spring 215 preloads the teeth of locking collar 212 into the teeth of locking plate 213. Locking collar 212 must be depressed to disengage from locking plate 213 in some embodiments. A main housing 216 encases internal components of ARD 210. A bearing retainer 217 encloses wave spring 218, which preloads the outer races of bearings 214 into main housing 216 to provide smooth bearing rotation. Wave spring 218 removes axial play in bearings 214 to increase rigidity and bearing life. A locknut 219 provides a preload against the inner races of bearings 214 from the right side thereof relative to FIG. 2B. A shim 220 made from a suitable material, such as bronze, deforms under compression from locknut 219 to provide a uniform preload to bearings 214.

FIG. 2C is a side cross-section view illustrating mechanical TL 230 of FIG. 2A, according to an embodiment of the present invention. TL 230 includes a housing 231 and a cover 232. Cover 232 is used for closing out the access necessary to measure the gap between housing 231 and bearing mount 238 that corresponds to the desired compression in spring 234. A spacer 233 is machined to provide the desired compression for spring 234. Balls 235 (in this embodiment, twelve of them in a ring) facilitate rotation. An input clutch 248 engages with shaft 211 to facilitate rotation of output shaft 236, which transmits output torque from TL 230.

A locknut 237 adjusts spring compression during calibration. Bearing mount 238 holds output shaft 236 in place with a single high capacity angular contact ball bearing 239. A debris shield 240 keeps spring 234 centered on output shaft 236 during rotation. An output clutch 242 engages and disengages power from output shaft 236. Torque transmission between output clutch 242 and output shaft 236 is accomplished via an involute spline. The involute spline allows the output clutch 242 to slide axially on output shaft 236 when the mechanism reaches its calibrated torque limit. A ball carrier 244 holds balls 235 in place. Two angular contact ball bearings 246, mounted in tandem, support input clutch 248 during rotation.

Figure 3A:
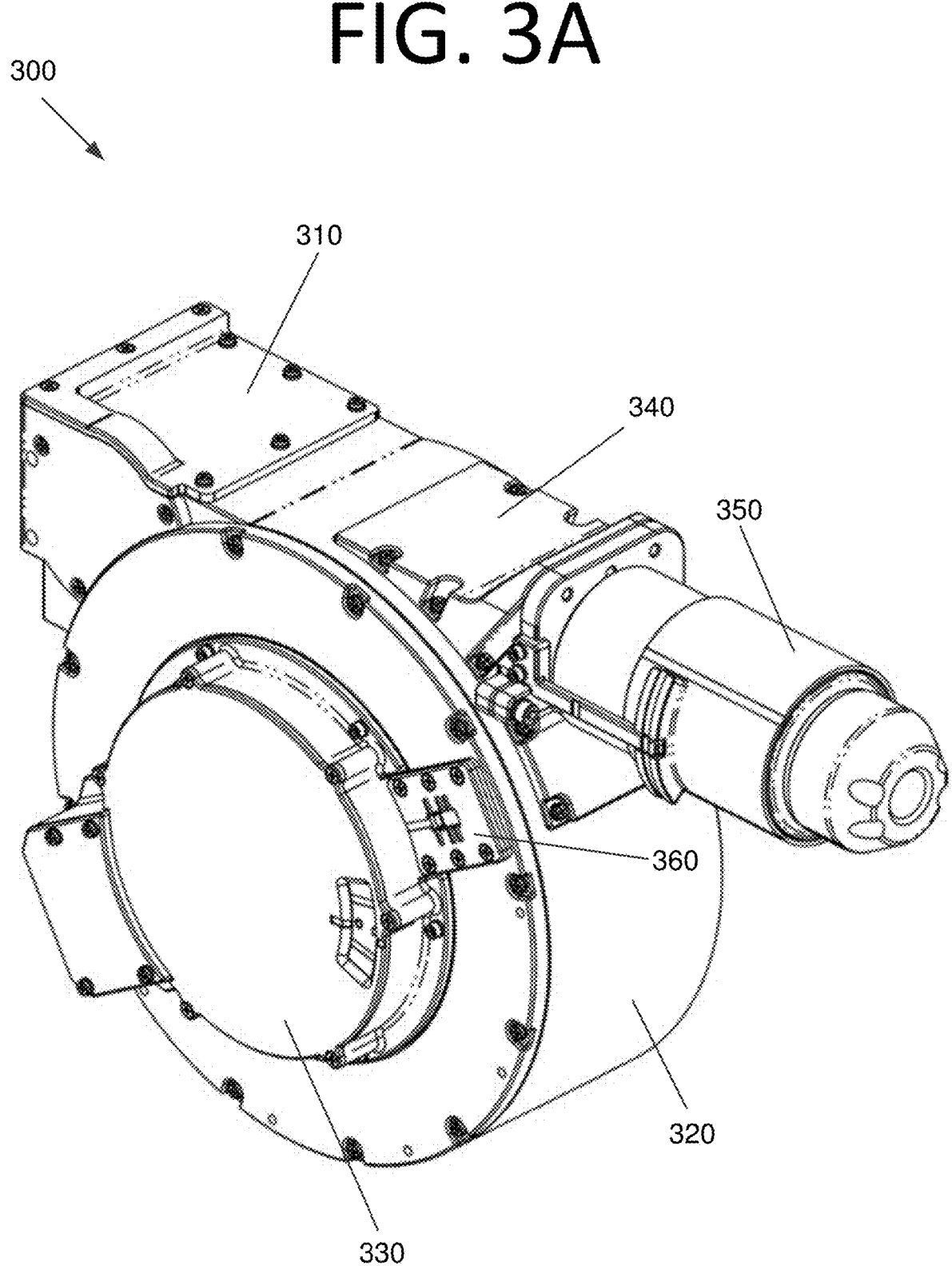
FIG. 3A is a right side perspective view illustrating a reel system, according to an embodiment of the present invention.
Figure 3B:
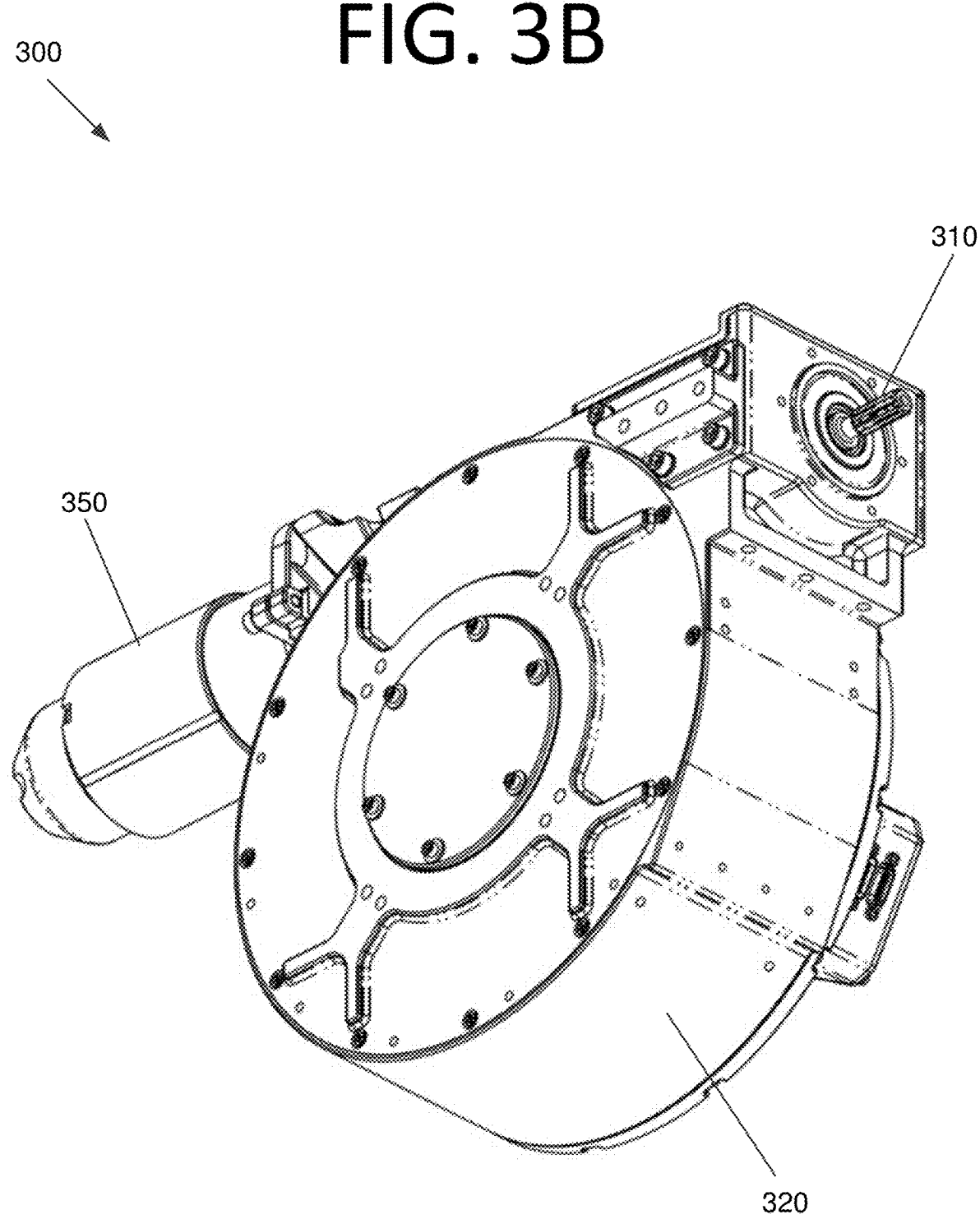
FIG. 3B is a left side perspective view illustrating the reel system, according to an embodiment of the present invention.

FIGS. 3A and 3B are right side and left side perspective views, respectively, of a reel system 300, according to an embodiment of the present invention. Reel system 300 includes a RAGB 310 that drives a rotating spool mechanism (not visible due to main housing 320) to extend/retract a VBA (not visible). Reel system 300 also includes a twist capsule 330 that contains a flex harness (not visible). The flex harness transmits signals from the VBA camera and tendon motors over the rotating interface. A funnel 340 guides deployment of the VBA. A seal system 350, mounted to the end of the funnel, actuates to form a seal at a service port and protects the VBA, which deploys through its center. Reel position indicators 360 (both fine and coarse) collectively show degrees of travel of the rotating mechanism and may be viewable by a fixed camera, such as FCA 140 of FIGS. 1A and 1B.

Figure 4B:
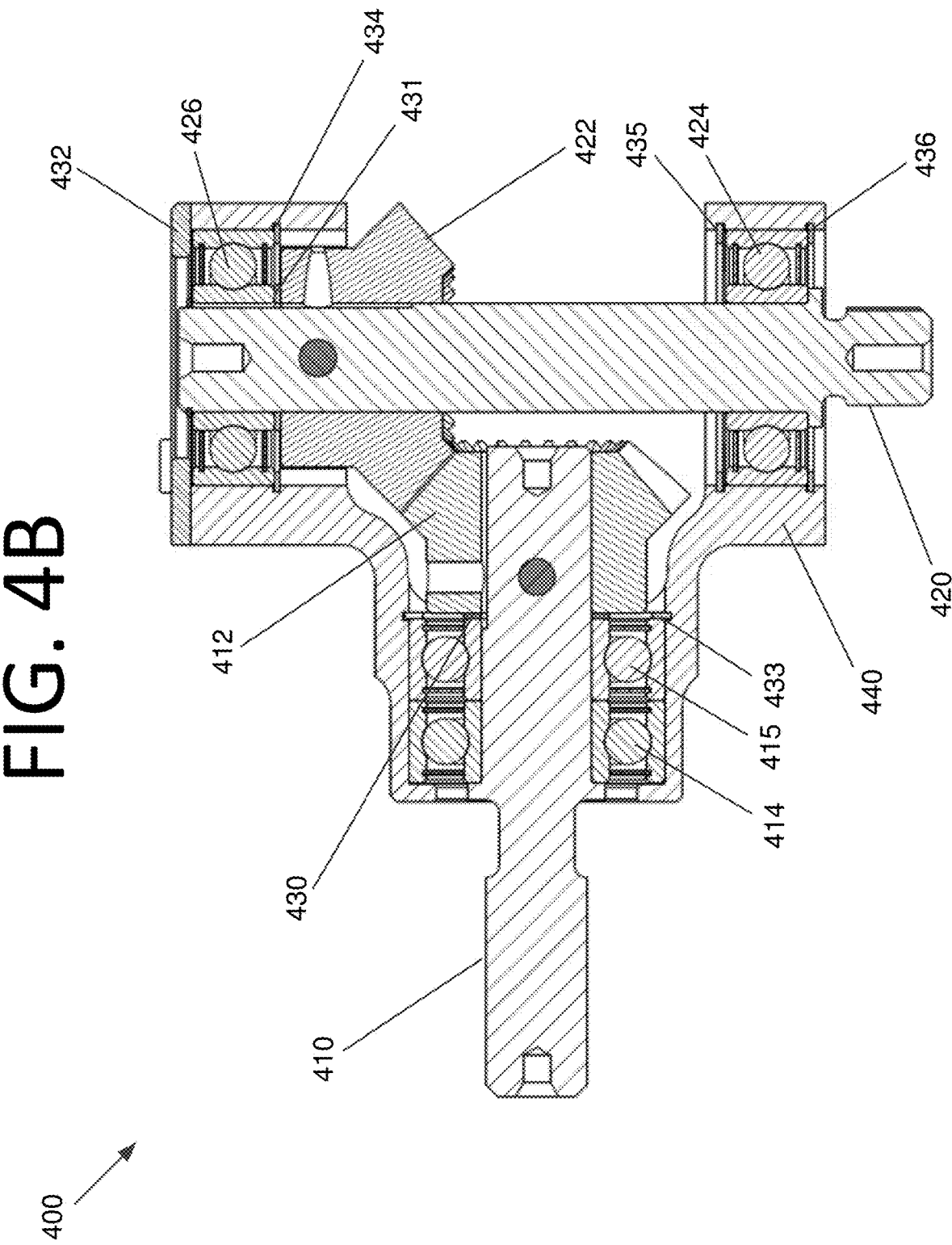
FIG. 4B is a cross-section view illustrating the RAGB, according to an embodiment of the present invention.

FIG. 4A is a perspective view and FIG. 4B is a cross-section view illustrating a RAGB 400, according to an embodiment of the present invention. RAGB 400 includes an input shaft 410 that engages with a drive mechanism and an output shaft 420 perpendicular to input shaft 410 that drives a pinion gear (see pinion gear 552 of FIG. 5B, for example). Involute splines are machined into shafts 410 and 420 to transmit torque into (shaft 410) and out of (shaft 420) RAGB 400. Miter gears 412 and 422 are also pinned, fastened, or otherwise integrally connected to respective shafts 410 and 420. Teeth of miter gear 412 mesh with miter gear 422 such that then the drive mechanism causes miter gear 412 to rotate via shaft 410, miter gear 422 also causes shaft 420 to rotate. Full complement radial ball bearings 414 and 415, and 424 and 426, help to facilitate rotation of shafts 410 and 420, respectively. Ball bearings 414 and 415 are tandem mounted on input shaft 410 and ball bearings 424 and 426 are straddle mounted on output shaft 420 to resist axial thrust forces generated by miter gears 412 and 422. Shims 430 and 431 help to properly mesh the teeth of miter gears 412 and 422 during assembly. A housing 440 houses components of RAGB 400. A close-out plate 432 and retaining rings 433, 434, 435, and 436 are installed to position and restrain the ball bearings inside housing 440.

Figure 5A:
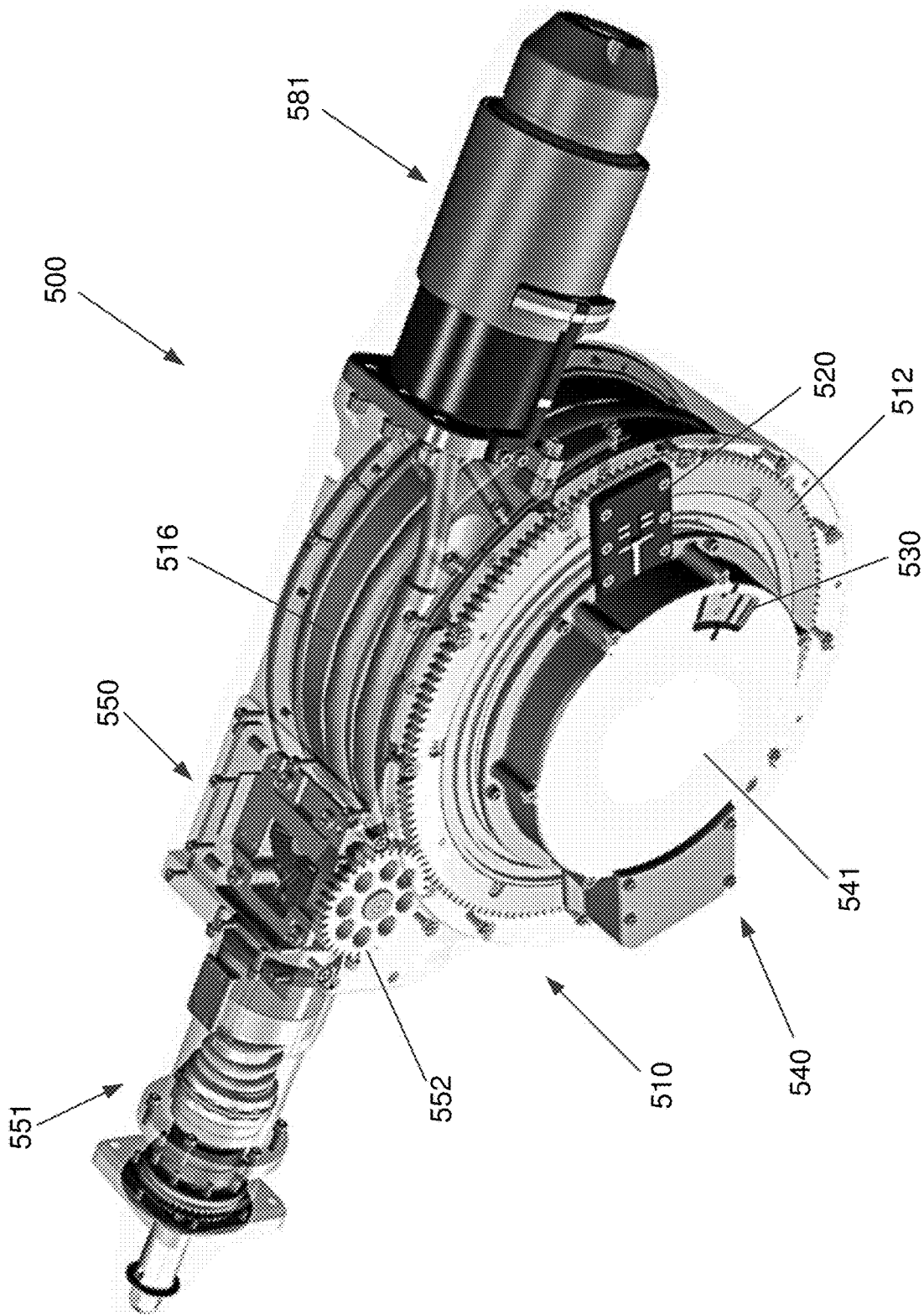
FIG. 5A is a semi-transparent right side perspective view illustrating a reel system, according to an embodiment of the present invention.

FIGS. 5A to 5H illustrate various views of a reel system 500 and its components, according to an embodiment of the present invention. FIG. 5A is a semi-transparent right side perspective view of reel system 500, which includes a rotating assembly 510 having a reel gear 512, a coarse reel position indicator 520, a fine reel position indicator 530, and a RAGB 550 (which may be RAGB 400 of FIGS. 4A and 4B in some embodiments) with a pinion gear 552. Reel system 500 is operably connected to a main drive assembly 551 (which may be main drive assembly 200 of FIG. 2A in some embodiments).

Coarse reel position indicator 520 and fine reel position indicator 530 may be viewable by a fixed camera (e.g., FCA 140 of FIG. 1B). A seal system 581 is configured to engage with a service port and allow a VBA 580 to pass through. RAGB 550 transfers rotation and torque from rotating assembly 551 to reel system 510 via pinion gear 552. More specifically, when pinion gear 552 is rotated via main drive assembly 551 and RAGB 550, teeth of pinion gear 552 that mesh with reel gear 512 cause reel gear 512 to rotate. This, in turn, rotates the entirety of rotating assembly 510 and fine reel position indicator 530. Coarse reel position indicator 520 translates in a linear direction as rotating assembly 510 rotates.

Rotating assembly 510 includes a spool 516, reel gear 512, a tendon management system (TMS) (see, e.g., FIGS. 6A and 6B), and a twist capsule 540 located within. A main housing 502 serves as the base structure for reel system 500 and provides a bearing interface for rotating assembly 510 and a rigid mechanical load interface back to the support structure (not shown). A funnel 582 guides deployment of VBA 580. A twist capsule 540 is affixed to rotating assembly 510, and includes an outer twist capsule 541 and an inner twist capsule 542.

Figure 5B:
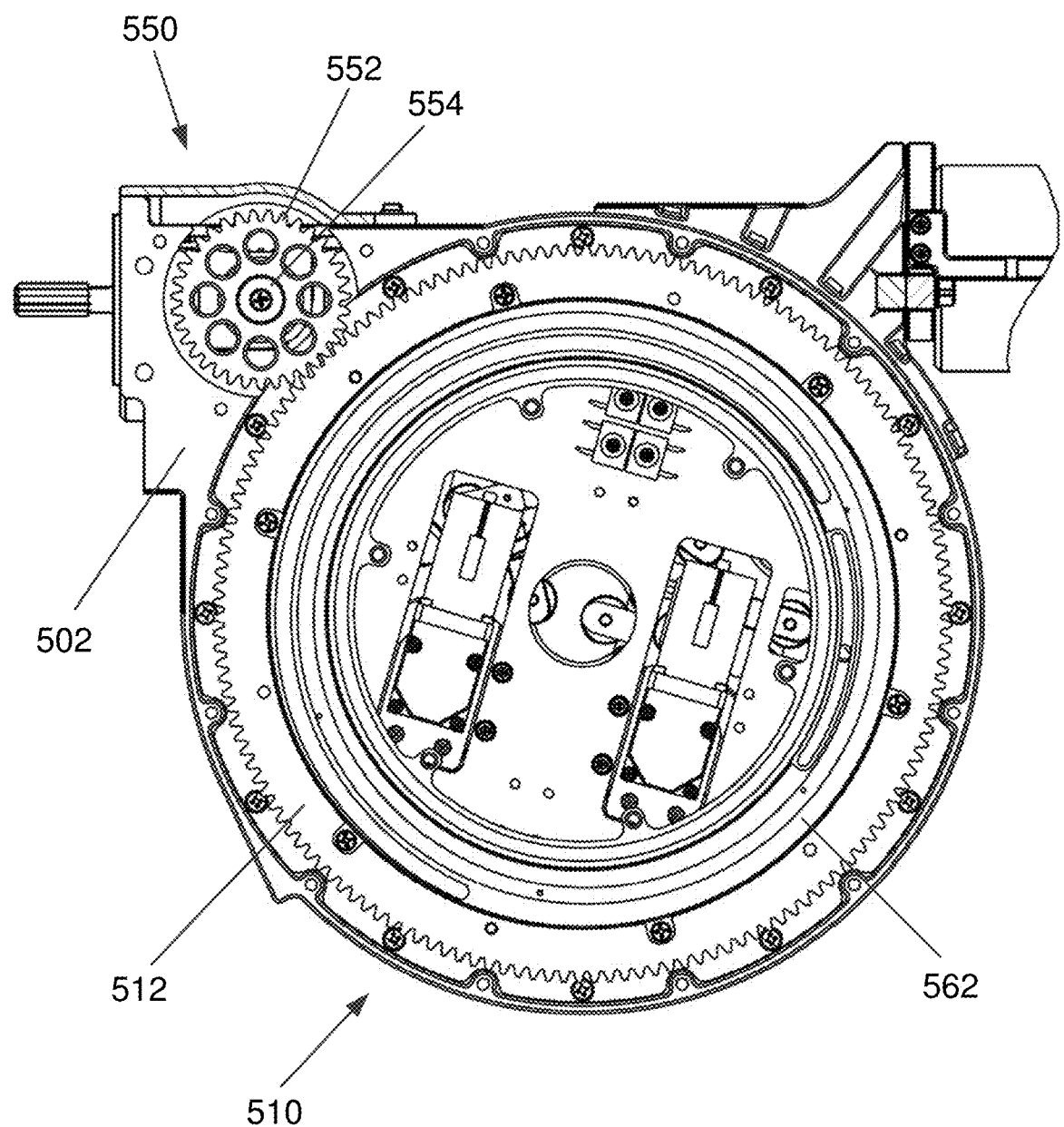
FIG. 5B is a side cross-section view illustrating the internal gear system within the reel system of FIG. 5A, according to an embodiment of the present invention.

Turning to FIG. 5B, the teeth of pinion gear 552 mesh with teeth of a reel gear 512 of reel system 500. Pinion gear 552 is driven by a pinion drive shaft 554 (which may be output shaft 420 of FIGS. 4A and 4B in some embodiments). Pinion gear 552, in turn, drives the rotation of reel gear 512, which is bolted, pinned, or otherwise operably connected to spool 516. A hardstop 560 rides within grooves of a hardstop track 562, which provides a predetermined amount of rotation. For instance, in some embodiments, hardstop track 562 contains a spiral groove that provides 570° of rotation and stops hardstop 560 at each end of travel. Hardstop track 562 is bolted, pinned, or otherwise operably connected to reel gear 512, and may be clockable to allow proper alignment of the spiral groove to a hardstop housing 514.

Figure 5C:
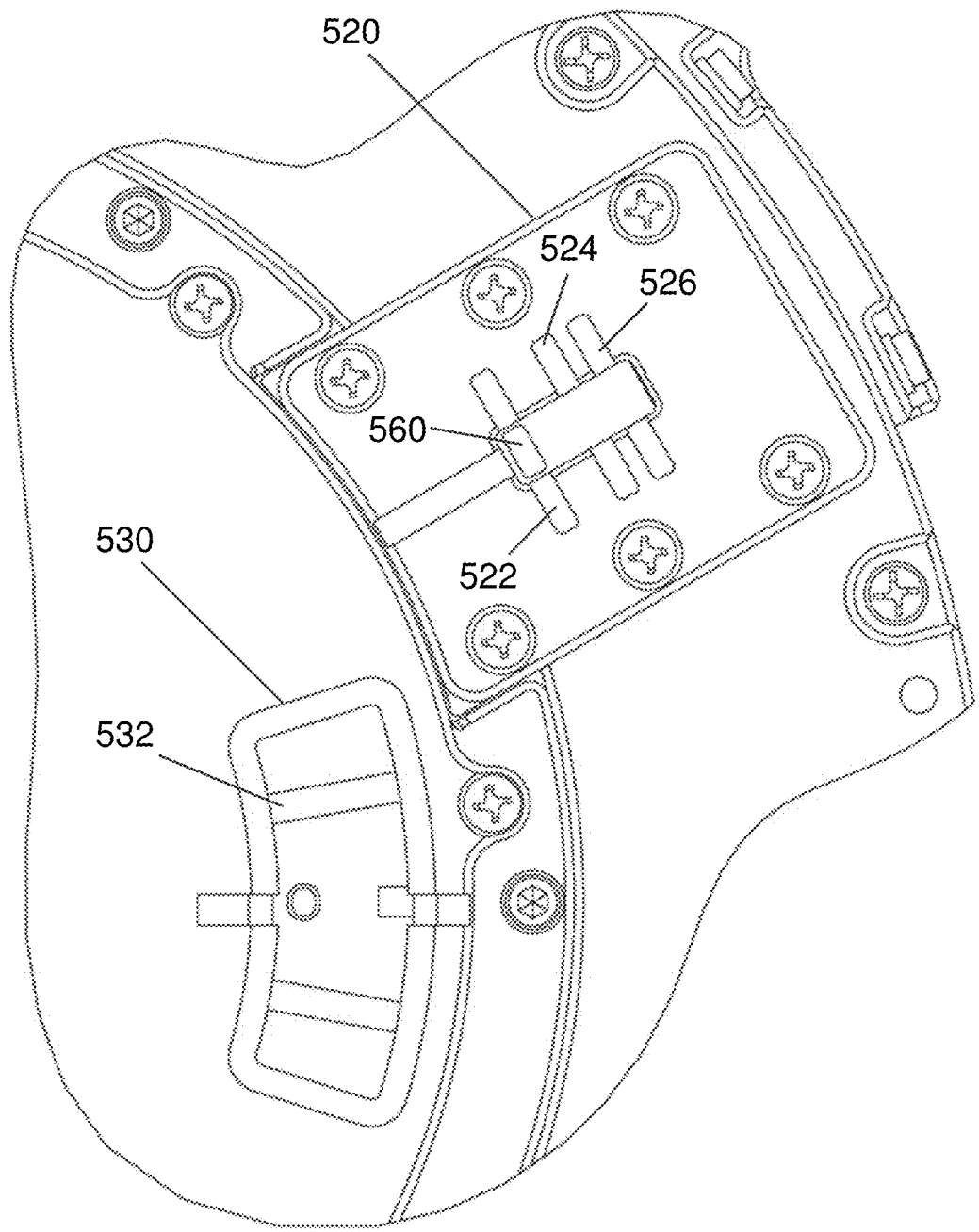
FIG. 5C is a magnified view illustrating the coarse and fine reel position indicators, according to an embodiment of the present invention.

FIG. 5C is a magnified view illustrating coarse reel position indicator 520 and fine reel position indicator 530, according to an embodiment of the present invention. Hardstop 560 moves linearly in conjunction with the rotating spiral groove of hardstop track 562. Angular marks 532 on fine reel position indicator 530 mark every 10° of reel system rotation. In some embodiments, 10° may indicate 0.625" of the deployment of VBA 580.

"Coarse" hash marks 522, 524, 526 mark the general deployment of VBA 580. For instance, in some embodiments, hash mark 522 may mark the fully retracted position of VBA 580 (i.e., 0°), hash mark 524 may mark one full turn of rotating assembly 510 (i.e., 360°), and hash mark 526 may mark the fully extended position of VBA 580 (e.g., 570°).

Figure 5D:
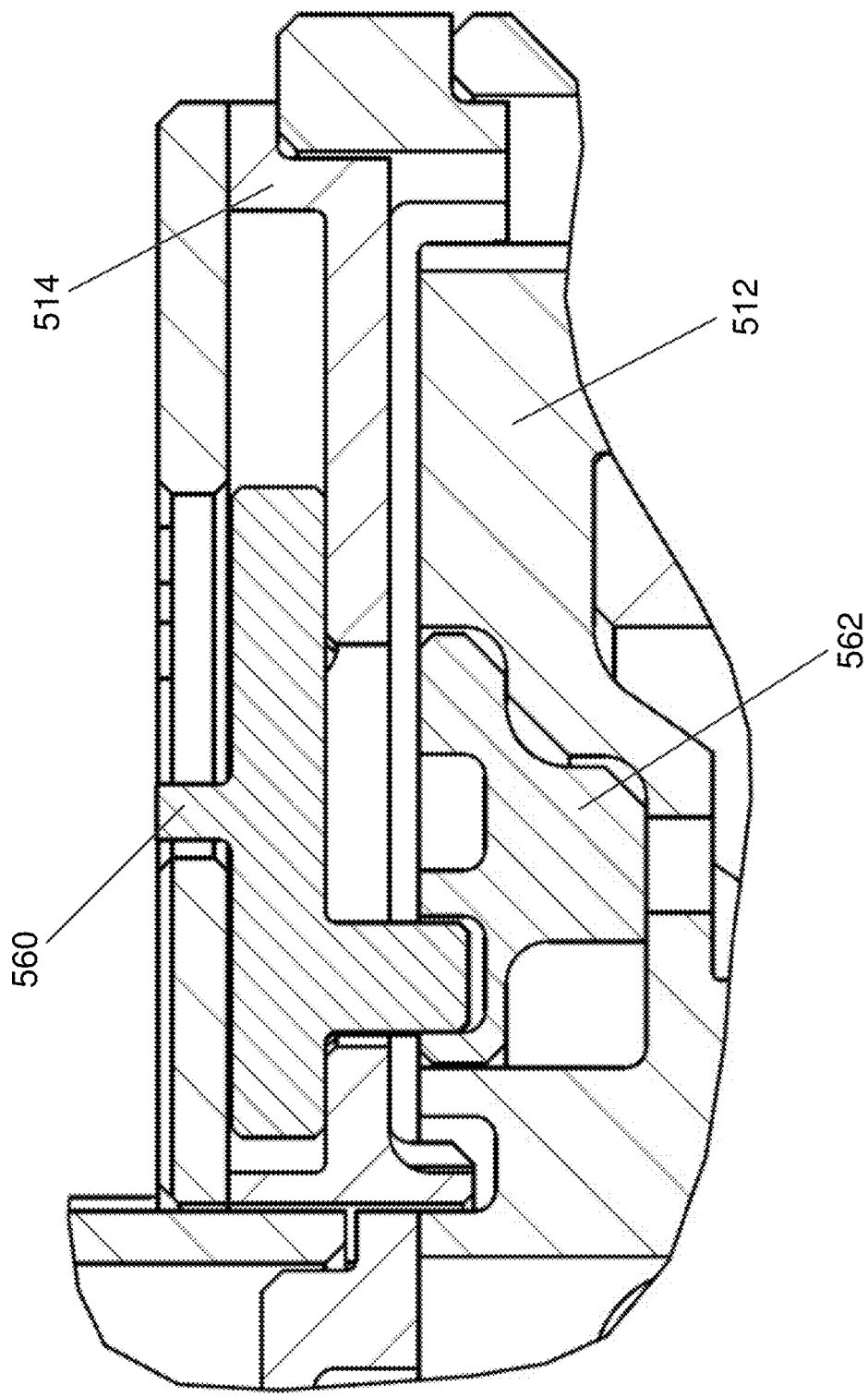
FIG. 5D is a side cross-section view illustrating the hardstop on the hardstop track, according to an embodiment of the present invention.

FIG. 5D is a side cross-section view illustrating hardstop 560 on hardstop track 562, according to an embodiment of the present invention. Hardstop 560 moves along spiral grooves in hardstop track 562. Linear motion of hardstop 560 is constrained by hardstop housing 514.

FIG. 5E is a side cross-section view illustrating internal components of reel system 500, according to an embodiment of the present invention. Spool 516 is housed within main housing 502 and provides the backbone of rotating assembly 510. Spool 516 rides on bearings 590 and contains VBA 580 within helical grooves and a tendon management system (not visible-see FIGS. 6A and 6B, for example) within the interior. VBA 580 is constrained between an inner volume 509 of main housing 502 and helical grooves of spool 516.

A rear cover 570 covers the back of rotating assembly 510 and facilitates a more favorable machining of main housing 502. A bearing retainer 594 is bolted to main housing 502 after spool 516 is installed within. A reel gear cover 572 covers and closes off the front side of rotating assembly 510. A labyrinth seal 574 minimizes the entry of contaminants from the environment.

Radial bearings 590 are large bore thin-section radial ball bearings in this embodiment to provide stable rotation. Radial ball bearings 590 are mounted face-to-face to provide accommodation of misalignment and resistance to exterior loading. Radial ball bearings 590 are shielded from contaminants on the sides facing VBA 580 by respective shields 596. O-rings 592 center radial ball bearings 590 in inner bore 509 while taking up a relatively large coefficient of thermal expansion (CTE) mismatch between radial ball bearings 590 (which may be steel, for instance) and housing 502 (which may be aluminum, for instance).

FIG. 5F is a top cross-section view of a portion of reel system 500 from which VBA 580 extends out from and is retracted back into reel system 500, according to an embodiment of the present invention. A funnel 582 includes a conical cavity 584 that is tangentially aligned with the helical groove of spool 516. Rotation of rotating assembly 510 acts to deploy VBA 580 into cavity 584 of funnel 582, and then out of seal system 581 (which is shown in more detail in FIG. 8A).

Cavity 584 of funnel 582 guides VBA 580 into seal system 581. In some embodiments, the interior sections of funnel 582 and seal system 581 that guide VBA 580 are plated or otherwise coated with a material that reduces friction during deployment, such as gold, nickel, or Teflon®. A straight section of seal system 581 ensures a normal trajectory of VBA 580 at the exit point.

Figure 5G:
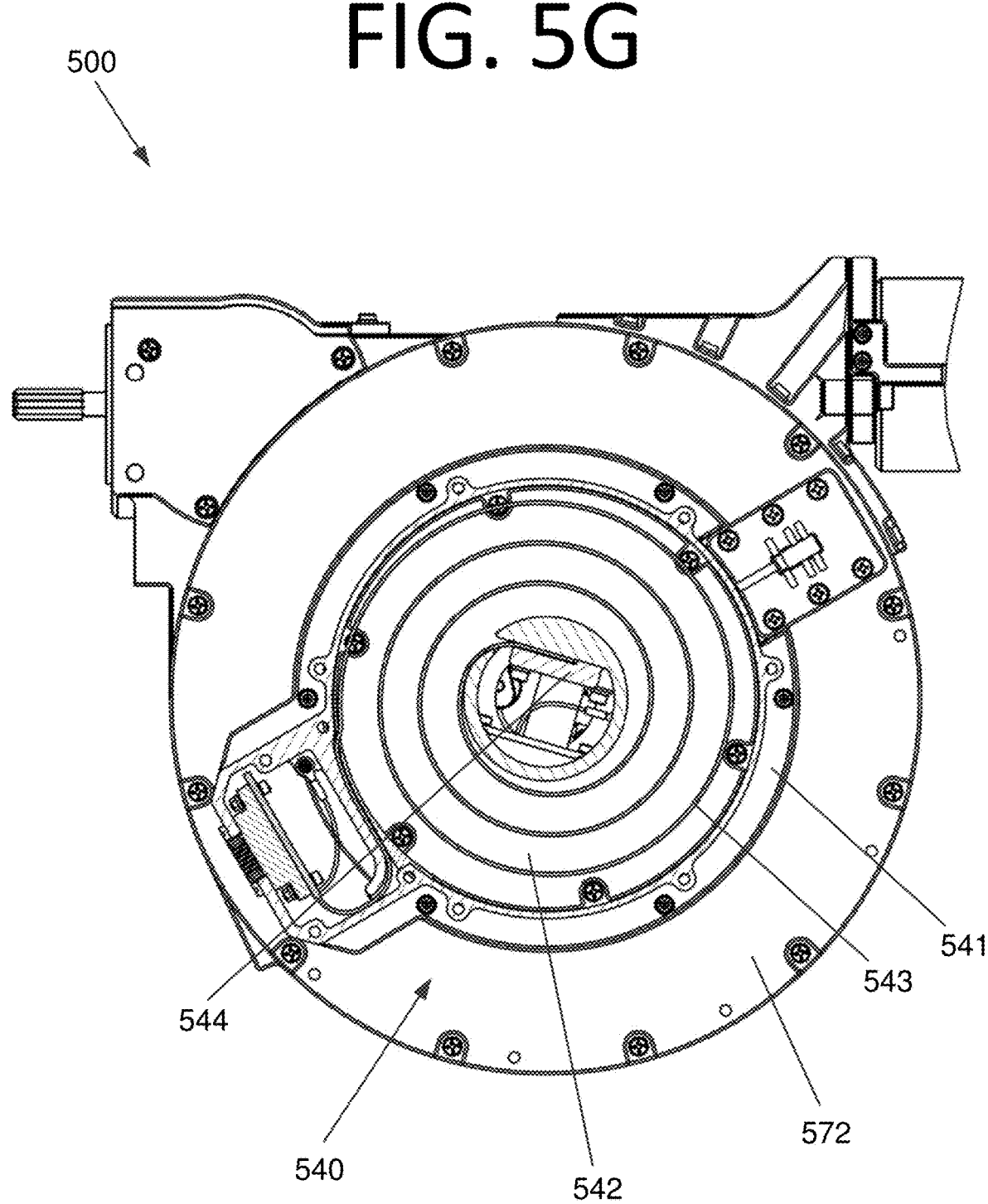
FIG. 5G is a right side cross-section view illustrating a twist capsule, according to an embodiment of the present invention.
Figure 5H:
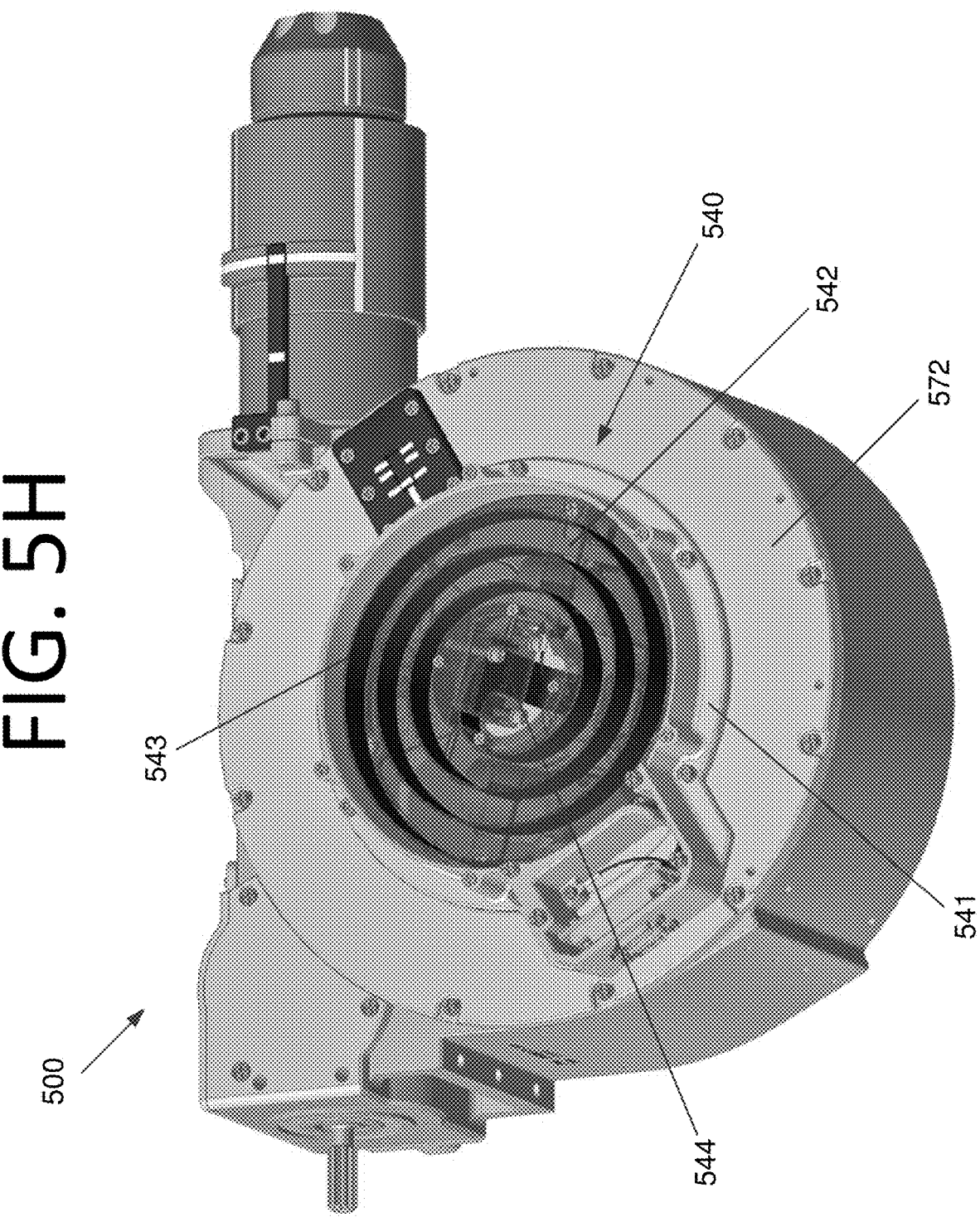
FIG. 5H is a right side semi-transparent perspective cutaway view illustrating the twist capsule, according to an embodiment of the present invention.

FIG. 5G is a right side cross-section view illustrating twist capsule 540 and FIG. 5H is a right side semi-transparent perspective cutaway view illustrating twist capsule 540, according to an embodiment of the present invention. In this embodiment, inner twist capsule 542 is bolted directly to reel gear 512 and rotates up to 570° as VBA 580 is deployed and retracted. One end of a spirally-wound flexible printed circuit board electrical (flex) harness 543 is affixed to an inner twist capsule 542, and connects to internal harnessing 544 that leads to the VBA camera and tendon motors (not shown). Outer twist capsule 541 is bolted directly to reel gear cover 572 and remains stationary while reel gear 512 and inner twist capsule 542 rotate. The other end of flex harness 543 is affixed to outer twist capsule 541, and connects to external harnessing leading to the MEB. As inner twist capsule 542 rotates, spirally-wound flex harness 543 winds and unwinds in the void between components of outer twist capsule 541 and inner twist capsule 542, allowing electrical signals to be transmitted over the rotating interface without interruption or loss of signal. Fine reel position indicator 530 is applied to the cover of inner twist capsule 542 as a decal in this embodiment after assembly and calibration of hardstop 560.

The VBA includes internal tendons that facilitate tendon-actuated tip articulation for the VBA camera at its tip. These tendons are controlled by a TMS, which is located within the rotating assembly of the reel system in some embodiments. Such a TMS 600 is shown in FIGS. 6A to 6D.

Figure 6B:
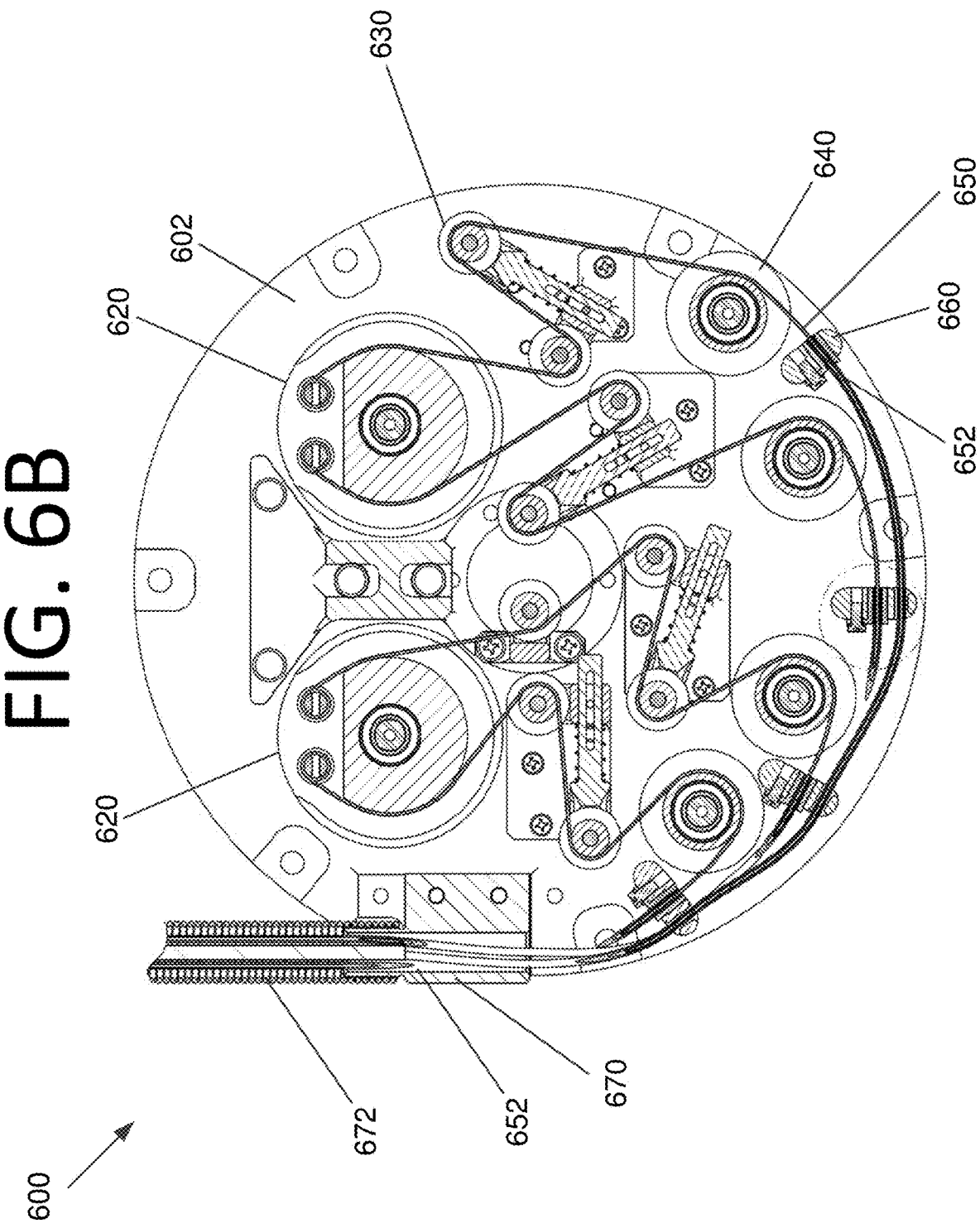
FIG. 6B is a top cross-section view illustrating the tendon layout within the TMS, according to an embodiment of the present invention.
Figure 6C:
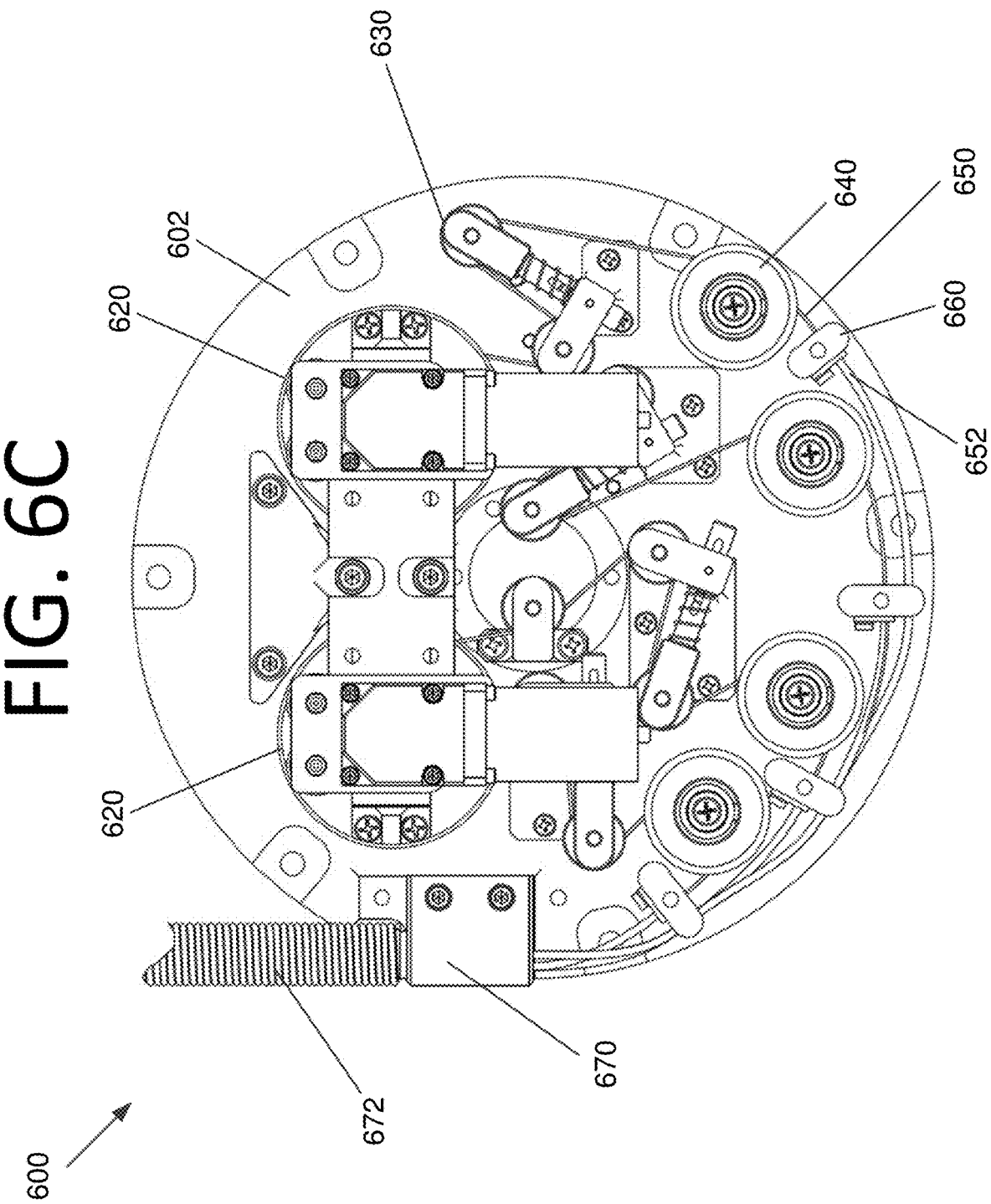
FIG. 6C is a top view illustrating the TMS, according to an embodiment of the present invention.

Referring to FIGS. 6A-C, tendon motors 610 are mounted on a motor mount 612, which provides a mounting interface for tendon motors 610. Tendon motors are used to actuate tendons 650 via respective drive pulleys 620. Drive pulleys 620 are the termination point for tendons 650. Two opposing tendons 650 terminate into each of drive pulleys 620 such that when a given drive pulley 620 rotates, one tendon tightens and the other tendon slackens.

Tensioner assemblies 630 are included for each respective tendon 650, and address excess tendon slackening. Tensioner assemblies 630 accommodate a full range of travel for a VBA 672. Each tensioner assembly includes two pulleys that tendon 650 rides on, one of which is on a spring-loaded arm. When tendon 650 is tensioned, tendon 650 pulls the arm back, compressing the spring. When tendon 650 is slackened, the spring pushes the arm back out, thereby taking up the potential slack in tendon 650.

Idler pulleys 640 guide tendons between support blocks 660 and tensioner assemblies 630. Support blocks 660 are also the point where tendons 650 enter guide tubes 652, which each house a respective tendon. Guide tubes 652, made of low friction and radiation resistant ethylene tetrafluoroethylene (ETFE) or similar material in some embodiments, are circumferentially bonded with a suitable adhesive to thru holes within the support blocks. Guide tubes 652 enter VBA 672 via a VBA mount 670, and are housed therein. All components of TMS 600 are mounted on a single mounting plate 602 in this embodiment.

FIG. 6D is a right side cross-section view illustrating a harness blockoff plate 680, according to an embodiment of the present invention. Harness blockoff plate 680 prevents harnessing from interfering with TMS 600 and provides mounting points for electrical connectors 684. Electrical connectors 684 facilitate transfer of electrical signals to and from tendon motors 610 (and in some embodiments, their respective temperature sensors).

The video borescope functionality of the VIPIR system is implemented by the VBA. The VBA of some embodiments features tremendous flexibility due to its coil spring construction. This construction may allow the VBA to passively flex beyond 360° while retaining the tip articulation capability. With this type of flexibility, the VBA is able to negotiate complex pipe systems with multiple sharp-angle turns. The flexibility also renders the VBA harmless to the system being traversed or inspected, as the body bends out of the way when it contacts structure.

The fully-deployed length allows the VBA to penetrate deep into otherwise inaccessible areas. The VBA may be deployed to any length between fully stowed and fully extended in some embodiments, with full video and articulation capability at all extension lengths. Additionally, the tip of the VBA is equipped with a small camera (e.g., a high definition (1280×720 pixel) camera with an integrated six-LED illumination array).

Through the use of a unique tendon mechanism, the tip of the VBA is able to articulate in any of four directions (+X, −X, +Y, −Y) in some embodiments. The directions are separated into two tendon pairs, where one pair drives articulation in the X direction, and the other pair drives articulation in the Y direction. The tendon pairs are arranged in a complimentary fashion onto a single drive pulley, such that rotation of the pulley places one tendon into compression, and the opposing member of the pair into slack. Counter-rotation of the pulley reverses the tension-slack balance. Simultaneous articulation in the X and Y directions is possible, as is articulation of the Y Direction while the X Direction is held at a non-zero angle (and vice-versa). The VBA is able to achieve equal to or better than 90° of articulation from the longitudinal axis in some embodiments.

Figure 7B:
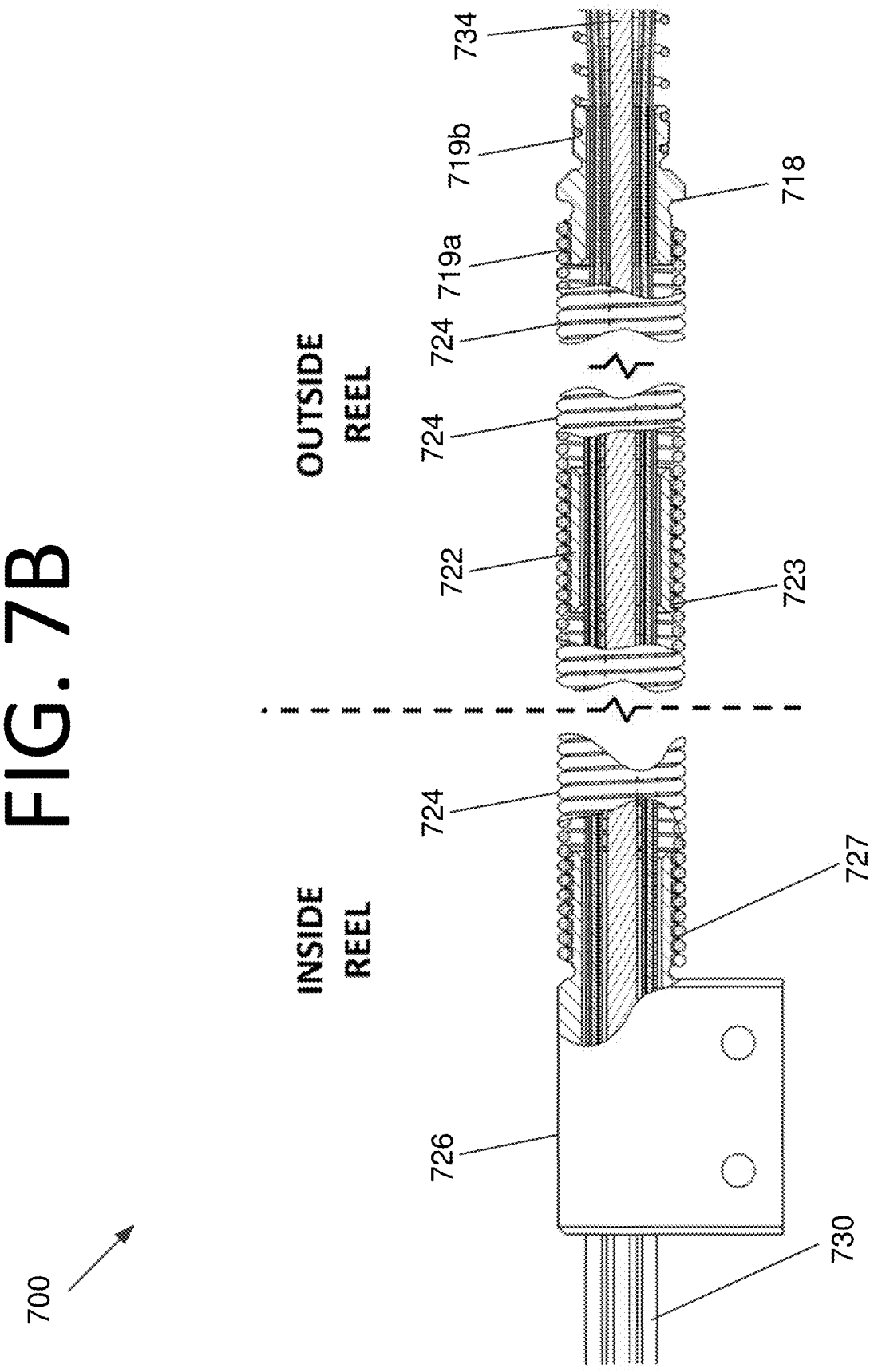
FIG. 7B is a segmented side cross-section view illustrating the VBA, according to an embodiment of the present invention.

Such a VBA 700 is shown in FIGS. 7A to 7E. As seen in FIG. 7A, for instance, VBA 700 is a "snake-camera" with an end that can bend to navigate through the interior of satellites and other spacecraft, for instance. VBA 700 is flexible along its entire length, enabling it to negotiate tight passages with changing directions. The distal end of VBA 700 (i.e., head 740) in this embodiment is able to articulate in four orthogonal directions via four tendons 716, and the range of motion is available at any deployed length. VBA 700 has an active section 710 that can be articulated once VBA 700 is deployed and a passive section 720 that is not articulated.

Active section 710 includes an active section bushing 712 that provides support for a compression spring 714. In some embodiments, active section bushing 712 is Teflon®-anodized, for example, to facilitate sliding of tendons 716. Tendons 716 are responsible for articulation of VBA 700. Active section 710 also includes a transition bushing 718 that provides a connection point between compression spring 714 and extension springs 724 of passive section 720. Active section 710 further includes a head 740 that serves as the leading edge of VBA 700, provides a termination point for tendons 716, and houses a VBA camera head 750.

Passive section 720 includes a passive section bushing 722 that provides a connection point between extension springs 724. Extension springs 724 help to maintain the centerline trajectory of VBA 700 in zero-g. A mount 726 provides a termination point of VBA 700 to the TMS. Guide tubes 730 from the TMS guide and protect tendons 716 within VBA 700.

Turning to FIG. 7B, mount 726, passive section bushing 722, and transition bushing 718 each include threaded sections 727, 723, and 719a, respectively, that match the relaxed pitch and profile of extension springs 724. Extension springs 724 may be threaded onto threaded sections 727, 723, and 719a and then be bonded into place. Guide tubes 730 and wiring harness 734 are free floating inside mount 726, extension springs, passive section bushing 722, and transition bushing 718.

Figure 7C:
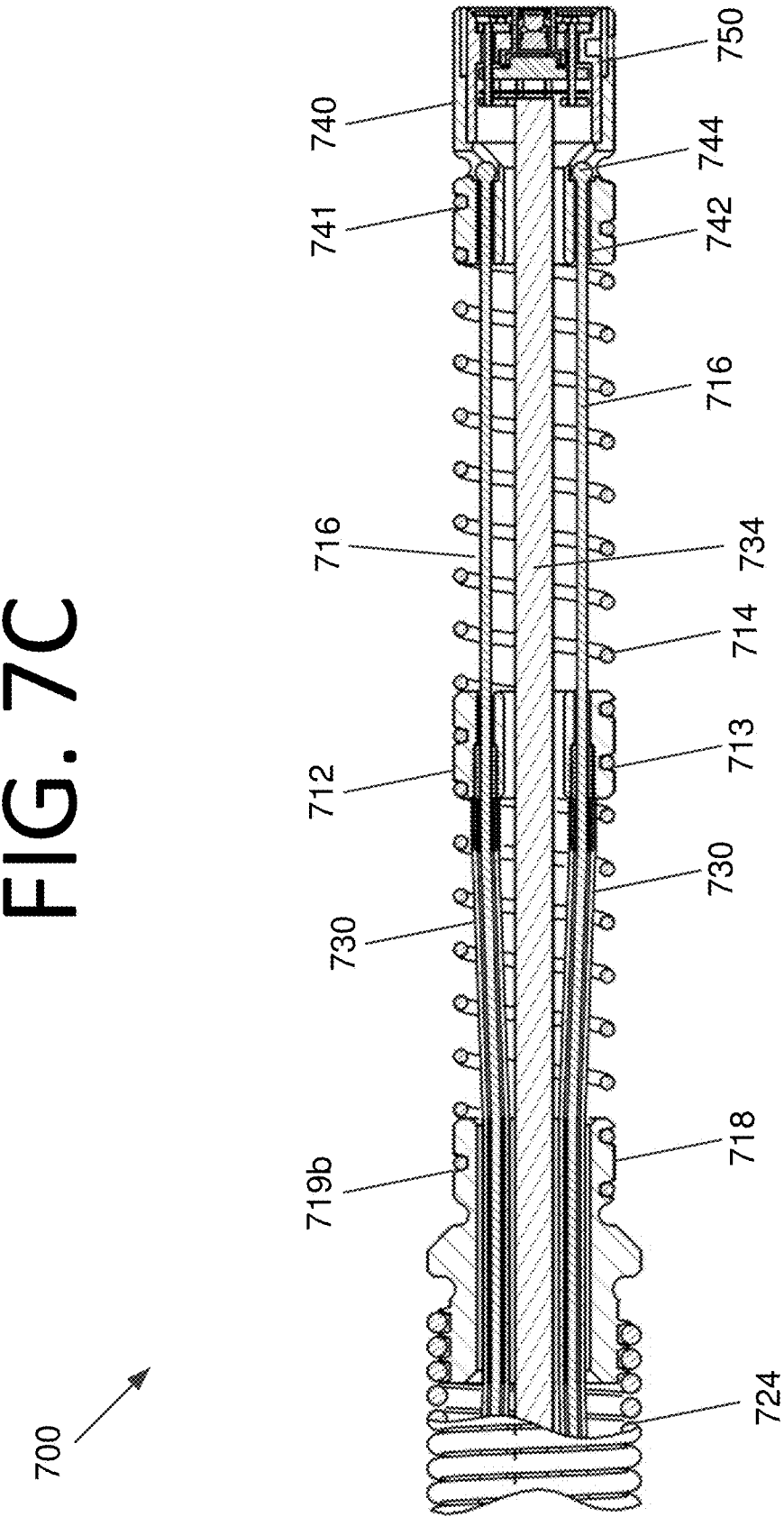
FIG. 7C is a side cross-section view illustrating the active section portion of the VBA, according to an embodiment of the present invention.

Turning to FIG. 7C, transition bushing 718 also has matching threads 719b for compression spring 714. Active section bushing 712 and head 740 also have matching threads 713 and 741, respectively, for compression spring 714. Each tendon 716 passes through a tendon termination bore 742 and ends in a knot 744 within head 740. Knots 744 may be staked in place using a suitable adhesive, for example.

Figure 7D:
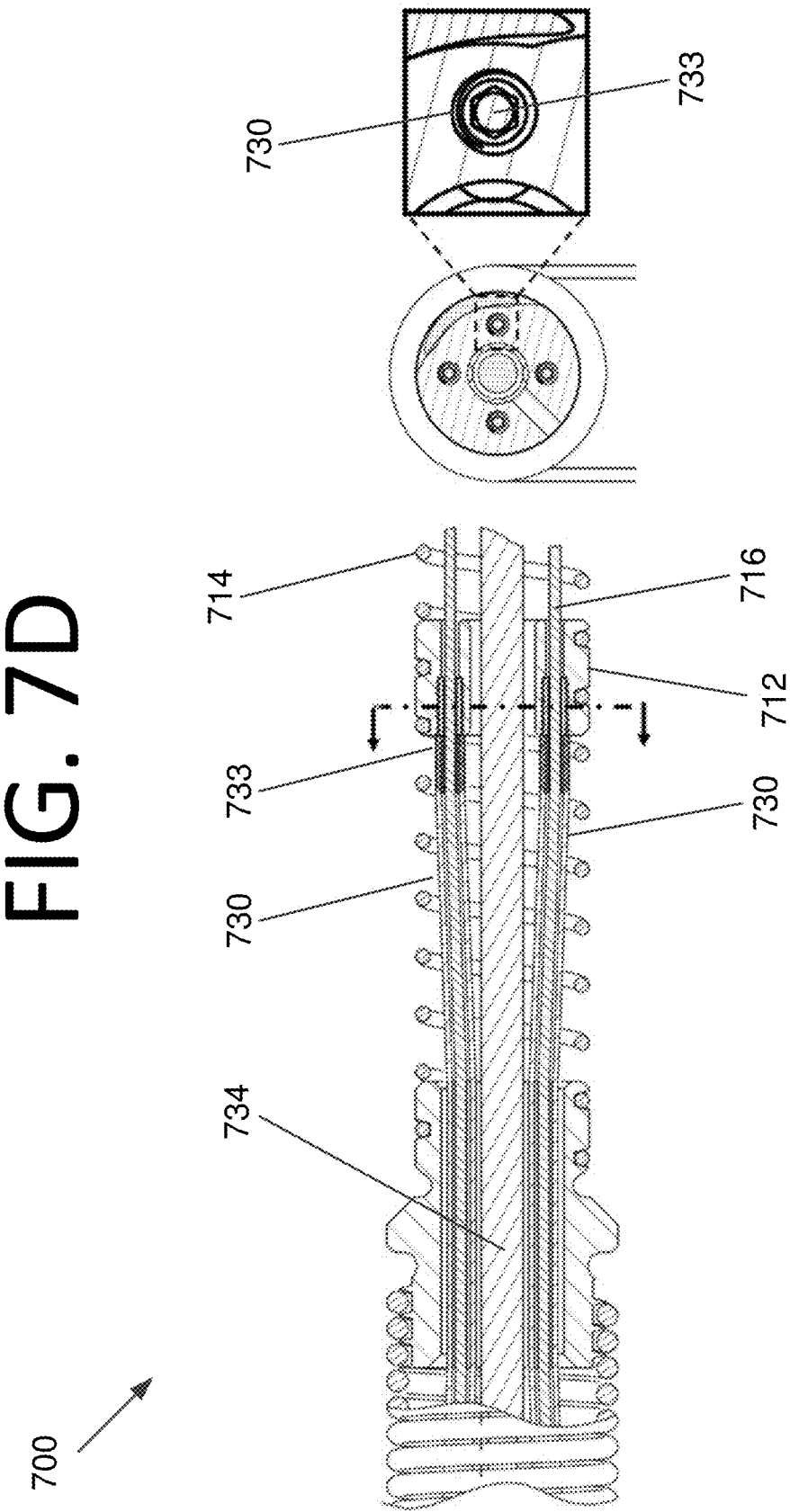
FIG. 7D is a cross-section view of a portion of FIG. 7C. The left portion more closely illustrates the guide tubes of the VBA, and the right portion illustrates a cross-section view of the active section bushing.

Turning to FIG. 7D, guide tubes 730 are threaded and bonded onto setscrews 733 that are installed into active section bushing 712. This facilitates a favorable packaging of the guide tube terminations within the tight space restrictions of active section 710. Because guide tubes 730 are terminated here, the aft portion of compression spring 714 acts as a compliance spring, taking up excess slackening of guide tubes 730 within passive section 720 as VBA 700 coils and uncoils. When VBA 700 is fully coiled, guide tubes 730 tubes are more constricted, and the compliance section compresses. When VBA 700 is fully uncoiled, guide tubes 730 are more relaxed, and the compliance section fully extends. This action prevents undue tensile stress on guide tubes 730.

Figure 7E:
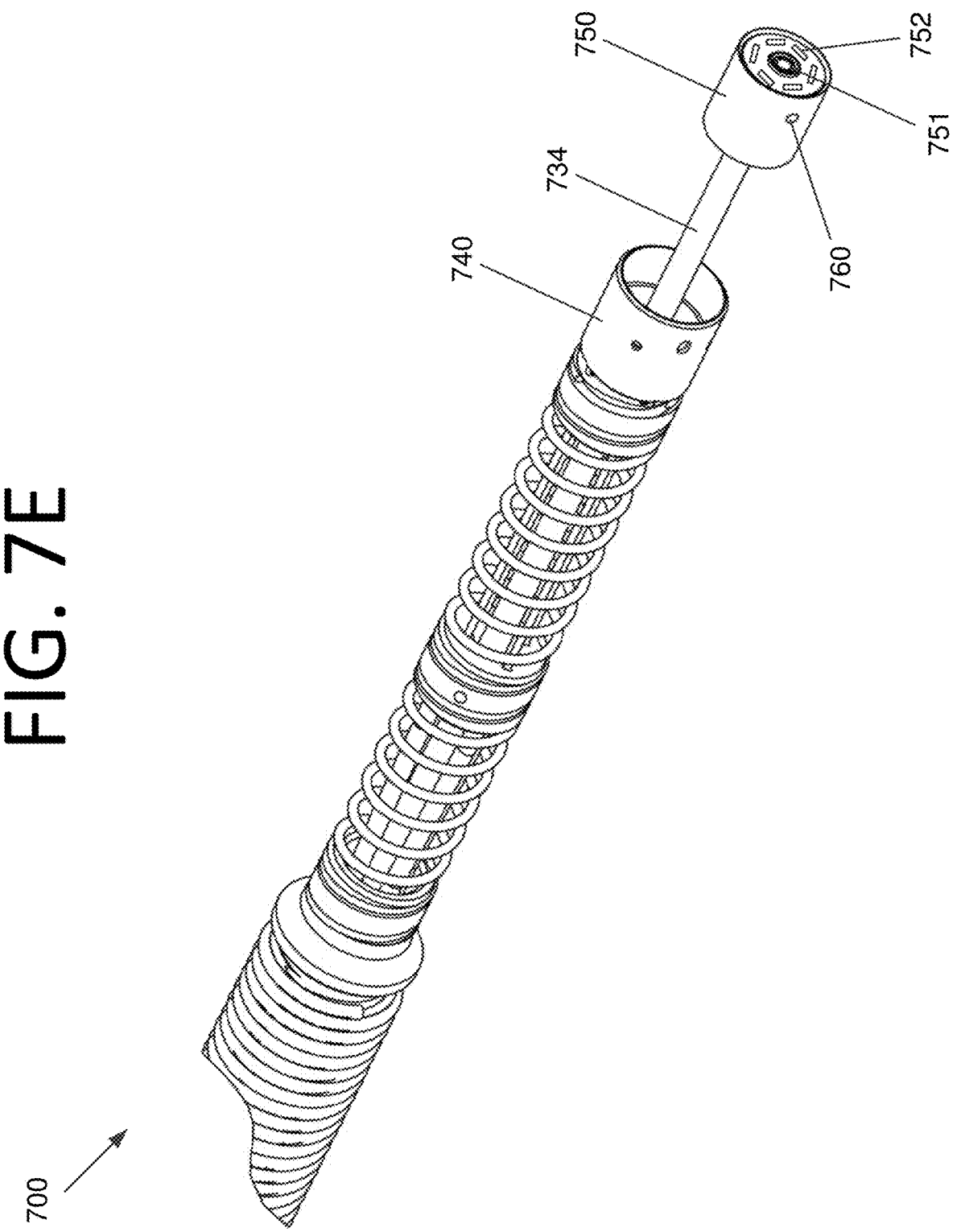
FIG. 7E illustrates a VBA camera head extended from a VBA head, according to an embodiment of the present invention.

FIG. 7E illustrates a VBA camera head 750 extended from head 740, according to an embodiment of the present invention. Camera head 750 may be significantly smaller than a United States dime in some embodiments. This, and the relatively small size of other components of VBA 700, may allow VBA 700 to be created with a relatively small size for insertion into relatively small service ports. In some embodiments, a thermocouple (not shown) may be bonded to camera head 750 and provides thermal telemetry.

Camera head 750 is housed within head 740, and is exposed at the end of head 740 via an opening. Camera head 750 includes a camera 751 and a miniature array of light emitting diodes (LEDs) 752 that provide light for camera 751 when deployed in dim or dark locations. In some embodiments, an alignment feature 760 in camera 750 may provide clocking to head 740, and thus a proper orientation between the view of camera 750 and the tendon directions. An integrated wiring harness 734 originates at the back of camera 750. This harness includes leads for LED power, video, and camera commanding, and is bound by polymeric tape, metallic shielding, and an exterior polymeric sheath in some embodiments. These sheathing layers provide protection for the wire leads housed within. The wires may be unsheathed along the portion that is within the active section of the VBA in order to facilitate greater flexibility during articulation of VBA 700.

Figure 8A:
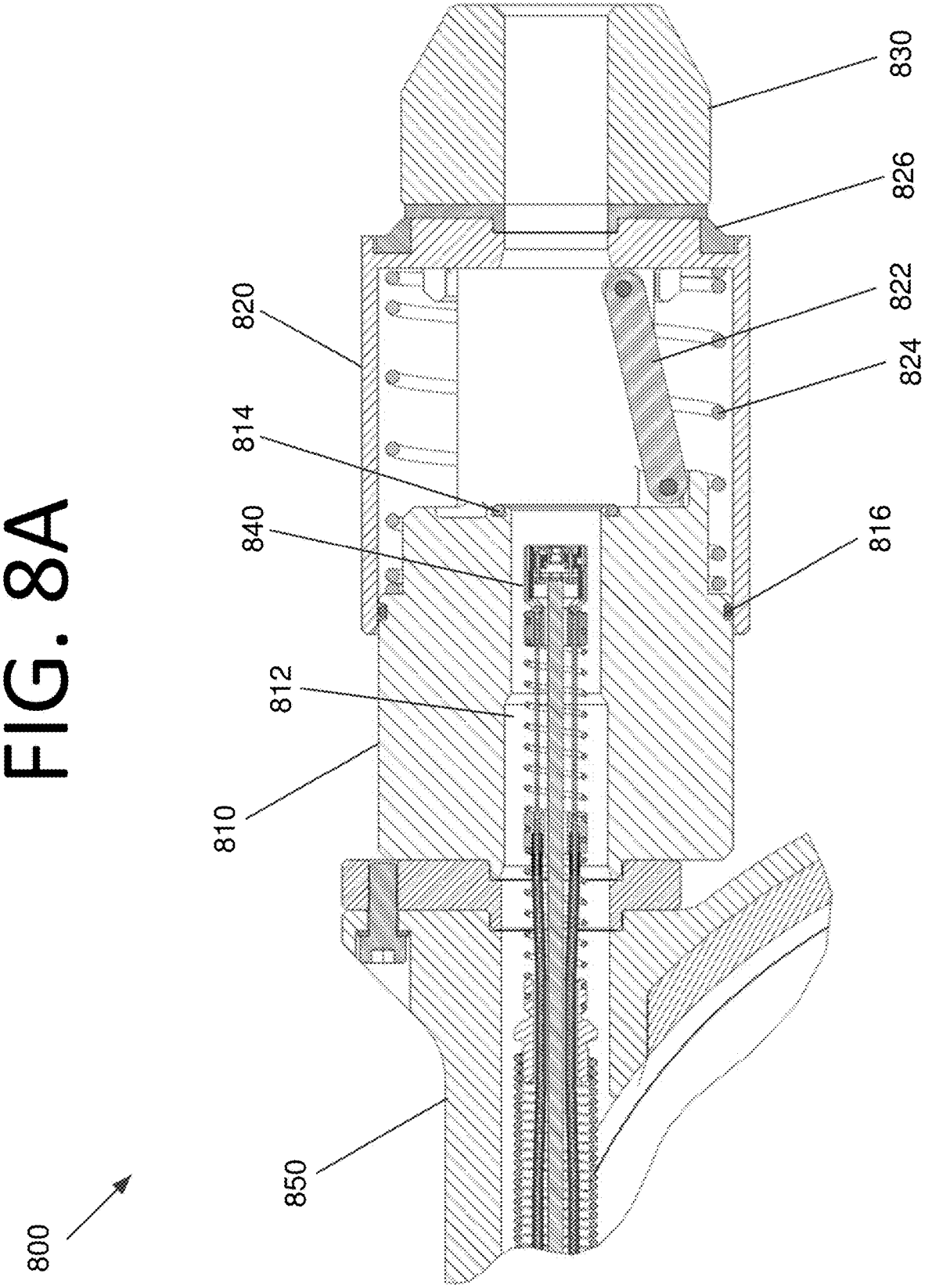
FIG. 8A is a side cross-section view illustrating a seal system, according to an embodiment of the present invention.
Figure 8B:
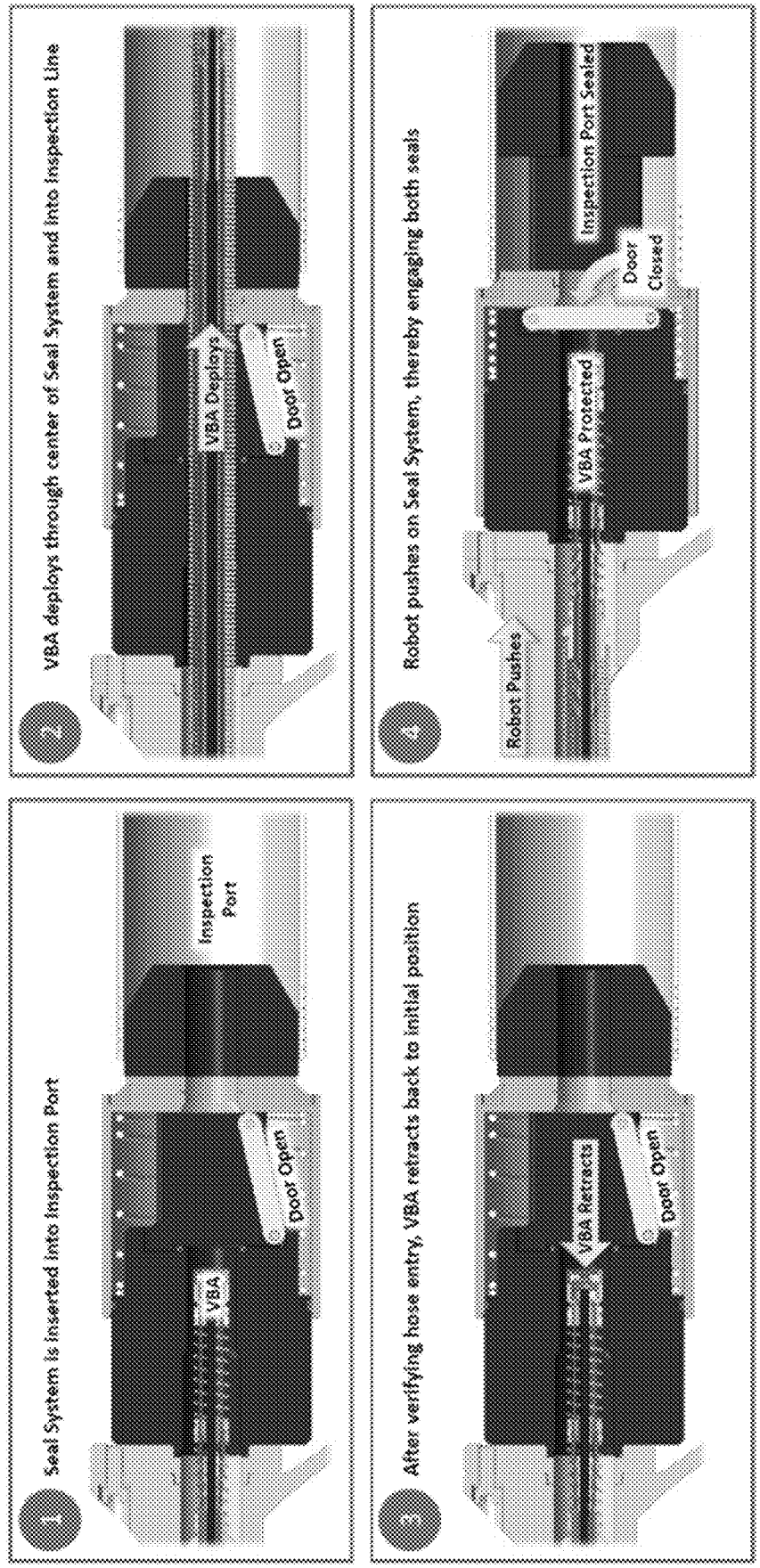
FIG. 8B is a side cutaway view illustrating the process for operating the seal system, according to an embodiment of the present invention.

In order to dock with a service port and deploy the VBA, some embodiments utilize a seal system. Such a seal system 800 and its operation are shown in FIGS. 8A and 8B, respectively. Seal system 800 includes a housing 810, an external seal carrier 820, and a nozzle 830. Housing 810 interfaces with a funnel 850 of a reel system and allows a VBA 840 to enter within via a housing cavity 812. An internal seal 814 seals VBA 840 within housing cavity 812 when it is in a retracted position and protects the camera of VBA 840. A radial seal 816 seals the gap between external seal carrier 820 and housing 810. An external seal 826 seals off the interior of a service port, when engaged.

Seal system 800 includes a door 822 that is open (as shown in FIG. 8A) when seal system 800 is not engaged with a service port and closed when seal system 800 is pressed against a service port with sufficient force (e.g., 25-30 pounds in some embodiments). When external seal carrier 820 is pressed against the service port, door 822 pivots and rolls up the internal surface of seal carrier 820 until door 822 is clamped between seal carrier 820 and housing 810, thereby compressing internal seal 814. A spring 824 biases external seal carrier 820 away from housing 810, allowing door 822 to open (via torsion springs) and allow passage of VBA 840. VBA 840 deploys through the center of seal system 800.

As illustrated by FIG. 8B, seal system 800 shown in step 1 in the upper left as being inserted into a service port with external seal carrier 820 fully extended and door 822 fully open. VBA 840 is then deployed into the service port, as shown in step 2 in the upper right. After the mission of VBA 840 is completed, VBA 840 is retracted back through seal system 800, as shown in step 3 in the lower left. The robot then pushes on the service port and door 822 closes, sealing against internal seal 814 and external seal 826, as shown in step 4 in the lower left.

Because VIPIR may be a video transmitting device in some embodiments, strictly-controlled electrical grounding may be required between components in order to ensure low-noise transmission of video back to the ground operator. VIPIR may incorporate unique surface coating combinations that allow it to achieve less than 2 milliohm resistance from the microfixture robotic interface to the rotating TMS, and less than 5 ohm resistance from the microfixture to the tip of the fully deployed VBA.

It will be readily understood that the components of various embodiments of the present invention, as generally described and illustrated in the figures herein, may be arranged and designed in a wide variety of different configurations. Thus, the detailed description of the embodiments of the present invention, as represented in the attached figures, is not intended to limit the scope of the invention as claimed, but is merely representative of selected embodiments of the invention.

The features, structures, or characteristics of the invention described throughout this specification may be combined in any suitable manner in one or more embodiments. For example, reference throughout this specification to "certain embodiments," "some embodiments," or similar language means that a particular feature, structure, or characteristic described in connection with the embodiment is included in at least one embodiment of the present invention. Thus, appearances of the phrases "in certain embodiments," "in some embodiment," "in other embodiments," or similar language throughout this specification do not necessarily all refer to the same group of embodiments and the described features, structures, or characteristics may be combined in any suitable manner in one or more embodiments.

It should be noted that reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized in certain embodiments that may not be present in all embodiments of the invention.

One having ordinary skill in the art will readily understand that the invention as discussed above may be practiced with steps in a different order, and/or with hardware elements in configurations which are different than those which are disclosed. Therefore, although the invention has been described based upon these preferred embodiments, it would be apparent to those of skill in the art that certain modifications, variations, and alternative constructions would be apparent, while remaining within the spirit and scope of the invention. In order to determine the metes and bounds of the invention, therefore, reference should be made to the appended claims.

The invention claimed is:

1. A visual inspection posable invertebrate robot (VIPIR) system, comprising:
a reel system comprising a main housing, a rotating assembly comprising a spool and a reel gear, and a tendon management system (TMS);
a video borescope assembly (VBA) that is operably connected to, and deployable by, the reel system, the VBA comprising a camera and a plurality of tendons; and
a seal system operably connected to the reel system, the seal system configured to engage with a service port and allow the VBA to pass therethrough.

2. The VIPIR system of claim 1, wherein the reel system comprises:
a right-angle gearbox (RAGB) operably connected to a main drive assembly, the RAGB comprising a pinion gear, wherein
the reel gear engages with the pinion gear of the RAGB and facilitates rotation of the spool, and
the RAGB is configured to rotate the reel gear, and thus the spool, via the pinion gear.

3. The VIPIR system of claim 1, wherein
the main housing further comprises an inner bore,
the spool comprises helical grooves, and
the VBA is constrained between the inner bore of the main housing of the reel system and the helical grooves of the spool.

4. The VIPIR system of claim 1, wherein the reel system further comprises a twist capsule, the twist capsule comprising:
an outer twist capsule operably connected to the main housing that remains stationary; and
an inner twist capsule within the outer twist capsule, wherein
the inner twist capsule is operably connected to the reel gear and rotates therewith,
the inner twist capsule is operably connected to an end of a flex harness, and
the twist capsule houses a spirally-wound flex harness.

5. The VIPIR system of claim 1, wherein the reel system comprises:
a coarse reel position indicator indicating coarse VBA deployment; and
a fine reel position indicator indicating fine VBA deployment, wherein
the coarse reel position indicator is configured to translate laterally when the spool rotates, and
the fine reel position indicator is configured to rotate with the spool.

6. The VIPIR system of claim 5, wherein
the reel system further comprises a hardstop track comprising spiral grooves, the hardstop track operably connected to the reel gear; and
the reel system further comprises a hardstop, wherein the hardstop rides within grooves of the hardstop track, which provides a predetermined amount of rotation.

7. The VIPIR system of claim 1, wherein the TMS further comprises:
at least one tendon motor; and
a respective drive pulley for each tendon motor, each drive pulley serving as a termination point for two tendons of the VBA, wherein
the at least one tendon motor is configured to actuate the plurality of tendons of the VBA via the respective drive pulleys, and
when a drive pully rotates, one connected tendon tightens and the other connected tendon slackens.

8. The VIPIR system of claim 7, wherein the TMS further comprises:
a tensioner assembly for each respective tendon of the VBA, each tensioner assembly accommodating a full range of travel of the respective tendon and accommodating a full range of travel for the VBA.

9. The VIPIR system of claim 8, wherein the TMS further comprises:
an idler pulley for each tendon; and
a support block for each tendon, the support block serving as a point where the tendon enters a guide tube, wherein the idler pulleys guide respective tendons between respective support blocks and respective tensioner assemblies.

10. The VIPIR system of claim 1, wherein the VBA further comprises:
a respective guide tube for each tendon;
an active section that can be articulated once the VBA is deployed, the active section comprising a head that houses the camera and provides a termination point for the tendons; and
a passive section that is not articulated, the passive section operably connected to the active section and the TMS.

11. The VIPIR system of claim 10, wherein the active section further comprises:
a compression spring;
an active section bushing that provides support for the compression spring; and
a transition bushing that provides a connection point between the compression spring and an extension spring of the passive section.

12. The VIPIR system of claim 10, wherein the passive section comprises:
extension springs that help to maintain a trajectory centerline of the VBA; and
a passive section bushing that provides a connection point between the extension springs.

13. The VIPIR system of claim 1, wherein the seal system comprises:
a housing comprising a housing cavity and an internal seal, wherein the internal seal retractably covers an opening in the housing cavity and the VBA enters within and passes through the housing cavity;
a door that is open when the seal system is not engaged with the service port and closes when the seal system is pressed against the service port with a predetermined force; and
an outlet through which the VBA can pass and enter the service port.

\* \* \* \* \*